US012714722B2

(12) United States Patent
Hockenbery et al.

(10) Patent No.: US 12,714,722 B2
(45) Date of Patent: Aug. 25, 2026

(54) CANCER COMBINATION THERAPIES UTILIZING A NICOTINAMIDE PHOSPHORIBOSYLTRANSFERASE INHIBITOR IN COMBINATION WITH A NICOTINAMIDE ADENINE DINUCLEOTIDE SALVAGE PATHWAY PRECURSOR

(71) Applicant: Fred Hutchinson Cancer Center, Seattle, WA (US)

(72) Inventors: David Hockenbery, Seattle, WA (US); Patrick Paddison, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 945 days.

(21) Appl. No.: 17/441,599

(22) PCT Filed: Mar. 20, 2020

(86) PCT No.: PCT/US2020/024019

§ 371 (c)(1),
(2) Date: Sep. 21, 2021

(87) PCT Pub. No.: WO2020/191359

PCT Pub. Date: Sep. 24, 2020

(65) Prior Publication Data

US 2022/0125814 A1 Apr. 28, 2022

Related U.S. Application Data

(60) Provisional application No. 62/821,821, filed on Mar. 21, 2019.

(51) Int. Cl.

| | |
|---|---|
| ***A61K 31/706*** | (2006.01) |
| ***A61K 31/437*** | (2006.01) |
| ***A61K 31/4409*** | (2006.01) |
| ***A61K 31/4439*** | (2006.01) |
| ***A61K 31/4545*** | (2006.01) |
| ***A61K 31/4725*** | (2006.01) |
| ***A61P 35/00*** | (2006.01) |

(52) U.S. Cl.

CPC .......... *A61K 31/706* (2013.01); *A61K 31/437* (2013.01); *A61K 31/4409* (2013.01); *A61K 31/4439* (2013.01); *A61K 31/4545* (2013.01); *A61K 31/4725* (2013.01); *A61P 35/00* (2018.01)

(58) Field of Classification Search

CPC ... C07D 213/56; A61P 35/00; A61K 2300/00; A61K 31/437; A61K 31/4439

See application file for complete search history.

(56) References Cited

U.S. PATENT DOCUMENTS

| | | | | |
|---|---|---|---|---|
| 8,106,184 | B2 | 1/2012 | Sauve et al. | |
| 8,197,807 | B2 | 6/2012 | Brenner | |
| 8,383,086 | B2 | 2/2013 | Brenner | |
| 9,302,989 | B2 | 4/2016 | Curtin et al. | |
| 9,335,332 | B2 | 5/2016 | Kumaravel et al. | |
| 9,382,267 | B2 | 7/2016 | Lee, Jr. et al. | |
| 10,000,519 | B2 | 6/2018 | Migaud et al. | |
| 10,000,520 | B2 | 6/2018 | Migaud et al. | |
| 10,144,742 | B2 | 12/2018 | Gigstad et al. | |
| 2006/0229265 | A1 | 10/2006 | Milburn et al. | |
| 2007/0117765 | A1 | 5/2007 | Sauve et al. | |
| 2012/0122924 | A1 | 5/2012 | Curtin et al. | |
| 2012/0251463 | A1* | 10/2012 | Brenner | A61P 3/06 424/48 |
| 2013/0109643 | A1 | 5/2013 | Riggins et al. | |
| 2013/0273034 | A1* | 10/2013 | Bair | A61P 29/00 514/274 |
| 2015/0353538 | A1 | 12/2015 | Willardsen et al. | |
| 2016/0075682 | A1 | 3/2016 | Genazzani et al. | |
| 2016/0229835 | A1 | 8/2016 | Burkholder et al. | |
| 2016/0272668 | A1 | 9/2016 | Dellinger et al. | |
| 2017/0189433 | A1 | 7/2017 | Szczepankiewicz et al. | |
| 2017/0204131 | A1 | 7/2017 | Szczepankiewicz et al. | |
| 2017/0210774 | A1 | 7/2017 | Carlson et al. | |
| 2018/0009784 | A1 | 1/2018 | Freeze et al. | |
| 2018/0086783 | A1 | 3/2018 | Carlson et al. | |
| 2018/0200275 | A1 | 7/2018 | Lawrence | |
| 2018/0362570 | A1 | 12/2018 | Ganapati et al. | |

FOREIGN PATENT DOCUMENTS

| | | | |
|---|---|---|---|
| CN | 104039762 | B | 11/2011 |
| CN | 105579449 | A | 10/2014 |
| EP | 2213288 | A1 | 4/2010 |
| EP | 3152220 | A1 | 4/2017 |
| JP | 2016532648 | A | 10/2016 |
| WO | WO2010002465 | A2 | 1/2010 |

(Continued)

OTHER PUBLICATIONS

Dondero (Oncoimmunology; 2016, vol. 5, No. 1, e1064578 (9 pages)).*

Tsigelny (Oncotarget, 2016, vol. 7, No. 33, 53074-53101).*

Hasmann (Cancer Research, 63, 7436-7442, 2003).*

Audrito, et al., "Nicotinaminde Phosphoribosyltransferase (NAMPT) as a Therapeutic Target in BRAF-Mutated Metastatic Melanoma," Journal of the National Cancer Institute, vol. 110, No. 3, 2017, pp. 290-303.

Estoppey, et al., "Identification of a novel NAMPT inhibitor by CRISPR/Cas9 chemogenomic profiling in mammalian cells," Scientific Reports, vol. 7, No. 42728, 2017, pp. 1-6.

Garavaglia, et al., "The high resolution crystal structure of periplasmic Haemophilus unfluenzae NAD nucleotidase reveals a novel enzymatic function of human CD73 related to NAD metablism," Biochem. J., vol. 441, 2012, pp. 131-141.

(Continued)

*Primary Examiner* — Pancham Bakshi

(74) *Attorney, Agent, or Firm* — C. Rachal Winger; Lee & Hayes PC

(57) ABSTRACT

Cancer combination therapies utilizing a nicotinamide phosphoribosyltransferase (NAMPT) inhibitor in combination with a nicotinamide adenine dinucleotide (NAD) salvage pathway precursor are described. Cancers treated with the combination therapies can be nicotinamide riboside kinase (NMRK1) low cancers and/or Myc high cancers and can include various forms of glioblastomas.

10 Claims, 8 Drawing Sheets

Specification includes a Sequence Listing.

(56) References Cited

FOREIGN PATENT DOCUMENTS

| | | | |
|---|---|---|---|
| WO | WO2010111111 | A1 | 9/2010 |
| WO | WO2012024478 | A2 | 2/2012 |
| WO | WO2012031197 | A1 | 3/2012 |
| WO | WO2012177782 | A1 | 12/2012 |
| WO | WO2014004884 | A1 | 1/2014 |
| WO | WO2017162840 | A1 | 12/2018 |
| WO | WO2018236814 | A2 | 12/2018 |

OTHER PUBLICATIONS

Neggers, et al., "Target identification of small molecules using large-scale CRISPR-Cas mutagenesis scanning of essential genes," Nat. Comm., vol. 9, No. 502, 2018, pp. 1-14.

Search Report and Written Opinion Dated Jun. 18, 2020 in International Application No. PCT/US2020/024019, 23 pages.

Pollak, et al., "Ion channel expression patterns in glioblastoma stem cells with functional and therapeutic implications for malignancy," PLoS One, vol. 12, No. 3, 2017, pp. 1-22.

Anders, et al., "HTSeq-a Python framework to work with high-throughput sequencing data," Bioinformatics, vol. 31, No. 2, 2015, pp. 166-169.

Beauparlant, et al., "Preclinical development of the nicotinamide phosphoribosyl transferase inhibitor prodrug GMX1777," Anticancer Drugs, vol. 20, No. 5, 2009, pp. 346-354.

Becher, et al., "Genetically Engineered Models Have Advantages over Xenografts for Preclinical Studies," Cancer Res., vol. 66, No. 7, 2006, pp. 3355-3359.

Bogan and Brenner, "Nicotinic acid, nicotinamide, and nicotinamide riboside: a molecular evaluation of NAD+ precursor vitamins in human nutrition," Annu. Rev. Nutr., vol. 28, 2008, pp. 115-130.

Boyer, et al., "Core transcriptional regulatory circuitry in human embryonic stem cells," Cell, vol. 122, No. 6, 2005, pp. 947-956.

Brennan, et al., "The somatic genomic landscape of glioblastoma," Cell, vol. 155, No. 2, 2013, pp. 462-477.

Bressan, et al., "Efficient CRISPR/Cas9-assisted gene targeting enables rapid and precise genetic manipulation of mammalian neural stem cells," Development, vol. 144, No. 4, 2017, pp. 635-648.

Brinkman, et al., "Easy quantitative assessment of genome editing by sequence trace decomposition," Nucleic. Acids. Res., vol. 42, No. 22, 2014, 8 pages.

Bruzzone, et al., "Catastrophic NAD+ depletion in activated T lymphocytes through Nampt inhibition reduces demyelination and disability in EAE," PLoS One., vol. 4, No. 11, 2009, 14 pages.

Butler, et al., "Integrating single-cell transcriptomic data across different conditions, technologies, and species," Nat. Biotechnol., vol. 36, No. 5, 2018, pp. 411-420.

Chen, et al., "G9a/GLP-dependent histone H3K9me2 patterning during human hematopoietic stem cell lineage commitment," Genes Dev., vol. 26, No. 22, 2012, pp. 2499-2511.

Chen, et al., "Homogeneous preparations of 3'-phosphoglycolate-terminated oligodeoxynucleotides from bleomycin-treated DNA as verified by electrospray ionization Fourier transform ion cyclotron resonance mass spectrometry," Anal. Biochem., vol. 289, No. 2, 2001, pp. 274-280.

Chi and Sauve, "Nicotinamide riboside, a trace nutrient in foods, is a vitamin B3 with effects on energy metabolism and neuroprotection," Curr. Opin. Clin. Nutr. Metab. Care., vol. 16, No. 6, 2013, pp. 657-661.

Dean, et al., "Identification of a putative Tdp1 inhibitor (CD00509) by in vitro and cell-based assays," J. Biomol. Screen., vol. 19, No. 10, 2014, pp. 1372-1382.

Ding, et al., "Cancer-Specific requirement for BUB1B/BUBR1 in human brain tumor isolates and genetically transformed cells," Cancer Discov., vol. 3, No. 2, pp. 198-211.

Ding, et al., "ZNF131 suppresses centrosome fragmentation in glioblastoma stem-like cells through regulation of HAUS5," Oncotarget, vol. 8, No. 20, 2017, pp. 48545-48562.

Fletcher, et al., "Nicotinamide riboside kinases display redundancy in mediating nicotinamide mononucleotide and nicotinamide riboside metabolism in skeletal muscle cells," Mol. Metab., vol. 6, No. 8, 2017, pp. 819-832.

Formentini, et al., " Detection and pharmacological modulation of nicotinamide mononucleotide (NMN) in vitro and in vivo," Biochem. Pharmacol., vol. 77, No. 10, 2009, pp. 1612-1620.

Franchetti, et al., "Stereoselective synthesis of nicotinamide beta-riboside and nucleoside analogs," Bioorg. Med. Chem. Lett., vol. 14, No. 18, 2004, pp. 4655-4658.

Galli, et al., "Isolation and characterization of tumorigenic, stem-like neural precursors from human glioblastoma," Cancer Res., vol. 64, No. 19, 2004, pp. 7011-7021.

Gebhardt, et al., "Myc regulates keratinocyte adhesion and differentiation via complex formation with Miz1," J. Cell. Biol., vol. 172, No. 1, 2006, pp. 139-149.

Happold, et al., "Does Valproic Acid or Levetiracetam Improve Survival in Glioblastoma? A Pooled Analysis of Prospective Clinical Trials in Newly Diagnosed Glioblastoma," J. Clin. Oncol., vol. 34, No. 7, 2016, pp. 731-739.

Hemmati, et al., "Cancerous stem cells can arise from pediatric brain tumors," PNAS, vol. 100, No. 25, 2003, pp. 15178-15183.

Herkert and Eilers, "Transcriptional repression: the dark side of myc," Genes Cancer, vol. 1, No. 6, 2010, pp. 580-586.

Herold, et al., "Negative regulation of the mammalian UV response by Myc through association with Miz-1," Mol. Cell, vol. 10, No. 3, 2002, pp. 509-521.

Holen, et al., "The pharmacokinetics, toxicities, and biologic effects of FK866, a nicotinamide adenine dinucleotide biosynthesis inhibitor," Invest New Drugs, vol. 26, No. 1, 2008, pp. 45-51.

Hollander, et al., "PTEN loss in the continuum of common cancers, rare syndromes and mouse models," Nat. Rev. Cancer, vol. 11, No. 4, 2011, pp. 289-301.

Hubert, et al., "Genome-wide RNAi screens in human brain tumor isolates reveal a novel viability requirement for PHF5A," Genes Dev., vol. 27, No. 9, 2013, pp. 1032-1045.

Hughes, et al., "Single-cell western blotting," Nat. Methods, vol. 11, No. 7, 2014, pp. 749-755.

Inamdar, et al., "Conversion of phosphoglycolate to phosphate termini on 3' overhangs of DNA double strand breaks by the human tyrosyl-DNA phosphodiesterase hTdp1," J. Biol. Chem., vol. 277, No. 30, 2002, pp. 27162-27168.

Jie, et al., "Activation of transient receptor potential vanilloid 4 induces apoptosis in hippocampus through downregulating PI3K/Akt and upregulating p38 MAPK signaling pathways," Cell Death Dis., vol. 6, No. 6, 2015, 8 pages.

Jungnickel, et al., "Phosphoinositide-dependent pathways in mouse sperm are regulated by egg ZP3 and drive the acrosome reaction," Dev. Biol., vol. 304, No. 1, 2007, pp. 116-126.

Kang, et al., "Single cell-resolution western blotting," Nat. Protoc., vol. 11, No. 8, 2016, pp. 1508-1530.

Kievit, et al., "Nanoparticle-mediated knockdown of DNA repair sensitizes cells to radiotherapy and extends survival in a genetic mouse model of glioblastoma," Nanomedicine, vol. 13, No. 7, pp. 2131-2139.

Lee, et al., "Tumor stem cells derived from glioblastomas cultured in bFGF and EGF more closely mirror the phenotype and genotype of primary tumors than do serum-cultured cell lines," Cancer Cell, vol. 9, No. 5, 2006, pp. 391-403.

Leslie and Hertog, "Mutant PTEN in Cancer: Worse Than Nothing," Cell, vol. 157, No. 3, 2014, pp. 527-529.

Liu, et al., "Synthesis of phosphodiester-type nicotinamide adenine dinucleotide analogs," Tetrahedron, vol. 65, 2009, pp. 8378-8383.

Metallo, et al., "Evaluation of 13C isotopic tracers for metabolic flux analysis in mammalian cells," J. Biotechnol., vol. 144, No. 3, 2009, pp. 167-174.

Mugabo, et al., "Identification of a mammalian glycerol-3-phosphate phosphatase: Role in metabolism and signaling in pancreatic ß-cells and hepatocytes," PNAS, vol. 113, No. 4, 2016, pp. 430-439.

Nikiforov, et al., "Pathways and subcellular compartmentation of NAD biosynthesis in human cells: from entry of extracellular

(56) References Cited

OTHER PUBLICATIONS precursors to mitochondrial NAD generation," J. Biol. Chem., vol. 286, No. 24, 2011, pp. 21767-2178.
O'Reilly, et al., "Temozolomide: a new oral cytotoxic chemotherapeutic agent with promising activity against primary brain tumours," Eur. J. Cancer, vol. 29A, No. 7, 1993, pp. 940-942.
Olesen, et al., "A preclinical study on the rescue of normal tissue by nicotinic acid in high-dose treatment with APO866, a specific nicotinamide phosphoribosyltransferase inhibitor," Mol. Cancer Ther., vol. 9, No. 6, 2010, pp. 1609-1617.
Olesen, et al., "Anticancer agent CHS-828 inhibits cellular synthesis of NAD," Biochem. Biophys. Res. Commun., vol. 367, No. 4, 2008, pp. 799-804.
Ostrom, et al., "CBTRUS Statistical Report: Primary Brain and Central Nervous System Tumors Diagnosed in the United States in 2008-2012," Neuro Oncol., vol. 17, No. 4, 2015, 62 pages.
Ozawa, et al., "Most human non-GCIMP glioblastoma subtypes evolve from a common proneural-like precursor glioma," Cancer Cell, vol. 26, No. 2, 2014, pp. 288-300.
International Report on Preliminary Patentability Dated Sep. 30, 2021 for International Application No. PCT/US2020/024019, 16 pages.
Pollard, et al., "Glioma stem cell lines expanded in adherent culture have tumor-specific phenotypes and are suitable for chemical and genetic screens," Cell Stem Cell, vol. 4, No. 6, 2009, pp. 568-580.
Povirk, Lawrence, "Processing of damaged DNA ends for double-strand break repair in mammalian cells," ISRN Mol. Biol., vol. 2012, No. 345805, 2012, 16 pages.
Rane, et al., "A novel orally bioavailable compound KPT-9274 inhibits PAK4, and blocks triple negative breast cancer tumor growth," Sci. Rep., vol. 7, No. 42555, 2017, 12 pages.
Ratajczak, et al., "NRK1 controls nicotinamide mononucleotide and nicotinamide riboside metabolism in mammalian cells," Nat. Commun., vol. 7, No. 13103, 2016, 12 pages.
Robinson, "edgeR: a Bioconductor package for differential expression analysis of digital gene expression data," Bioinformatics, vol. 26, No. 1, 2010, pp. 139-140.
Robinson, et al., "edgeR: a Bioconductor package for differential expression analysis of digital gene expression data," Bioinformatics, vol. 26, No. 1, 2010, pp. 139-140.
Sampath, et al., "Inhibition of nicotinamide phosphoribosyltransferase (NAMPT) as a therapeutic strategy in cancer," Pharmacol Ther., vol. 151, 2015, pp. 16-31.
Sanjana, et al., "Improved vectors and genome-wide libraries for CRISPR screening," Nat. Methods, vol. 11, No. 8, 2014, pp. 783-784.
Schaniel, et al., "Smarcc1/Baf155 couples self-renewal gene repression with changes in chromatin structure in mouse embryonic stem cells," Stem Cells, vol. 27, No. 12, 2009, pp. 2979-2791.
Segerer, et al., "An essential developmental function for murine phosphoglycolate phosphatase in safeguarding cell proliferation," Sci. Rep., vol. 6, No. 35160, 2016, 13 pages.
Seifried, et al., "Reversible oxidation controls the activity and oligomeric state of the mammalian phosphoglycolate phosphatase AUM," Free Radic Biol Med., vol. 97, 2016, pp. 75-84.
Singh, et al., "Identification of human brain tumour initiating cells," Nature, vol. 432, No. 7015, 2004, pp. 396-401.
Singh, et al., "Identification of a cancer stem cell in human brain tumors," Cancer Res., vol. 63, No. 18, 2003, pp. 5821-5828.
Stupp, et al., "Radiotherapy plus concomitant and adjuvant temozolomide for glioblastoma," N. Engl J. Med., vol. 352, No. 10, 2005, pp. 987-996.
Sturm, et al., "New Brain Tumor Entities Emerge from Molecular Classification of CNS-PNETs," Cell, vol. 164, No. 5, 2016, pp. 1060-1072.
Szeliga, et al., "Lack of expression of the liver-type glutaminase (LGA) mRNA in human malignant gliomas," Neurosci Lett., vol. 374, No. 3, 2005, pp. 171-173.
Tanimori, et al., "An efficient chemical synthesis of nicotinamide riboside (NAR) and analogues," Bioorg. Med. Chem. Lett., vol. 12, No. 8, 2002, pp. 1135-1137.
Tian, et al., "Activation of Transient Receptor Potential Vanilloid 4 Impairs the Dendritic Arborization of Newborn Neurons in the Hippocampal Dentate Gyrus through the AMPK and Akt Signaling Pathways," Front Mol. Neurosci., vol. 29, No. 7, 1993, pp. 940-942.
Toledo, et al., "Genome-wide CRISPR-Cas9 Screens Reveal Loss of Redundancy between PKMYT1 and WEE1 in Glioblastoma Stem-like Cells," Cell Rep., vol. 13, No. 11, 2015, pp. 2425-2439.
Trammell and Brenner, "Targeted, LCMS-based Metabolomics for Quantitative Measurement of NAD(+) Metabolites," Comput. Struct. Biotechnol J., vol. 4, No. 5, 2013, 9 pages.
Trammell, et al., "Nicotinamide riboside is uniquely and orally bioavailable in mice and humans," Nat. Commun., vol. 7, No. 12948, 2016, 14 pages.
Trapnell, et al., "Differential gene and transcript expression analysis of RNA-seq experiments with TopHat and Cufflinks," Nat. Protoc., vol. 7, No. 3, 2012, pp. 562-578.
Verhaak, et al., "Integrated genomic analysis identifies clinically relevant subtypes of glioblastoma characterized by abnormalities in PDGFRA, IDH1, EGFR, and NF1," Cancer Cell, vol. 17, No. 1, 2010, pp. 98-110.
Von Heideman, et al,, "Safety and efficacy of NAD depleting cancer drugs: results of a phase I clinical trial of CHS 828 and overview of published data," Cancer Chemother Pharmacol, vol. 65, No. 6, 2010, pp. 1165-1172.
Wang, et al., "Allele-specific tumor spectrum in pten knockin mice," PNAS USA, vol. 7 No. 11, 2010, pp. 5142-5147.
Wang, et al., "Tumor Evolution of Glioma-Intrinsic Gene Expression Subtypes Associates with Immunological Changes in the Microenvironment," Cancer Cell, vol. 32, No. 1, 2017, pp. 42-56.
Wolman, et al., "A genome-wide screen identifies PAPP-AA-mediated IGFR signaling as a novel regulator of habituation learning," Neuron, vol. 82, No. 6, 2015, pp. 1200-1211.
Yang, et al., "Syntheses of nicotinamide riboside and derivatives: effective agents for increasing nicotinamide adenine dinucleotide concentrations in mammalian cells," J. Med. Chem., vol. 50, No. 26, 2007, pp. 6458-6461.
Ye and Tu, "Sink into the Epigenome: Histones as Repositories That Influence Cellular Metabolism," Trends Endocrinol Metab., vol. 29, No. 9, 2018, 262-237.
Zabka, et al., "Retinal toxicity, in vivo and in vitro, associated with inhibition of nicotinamide phosphoribosyltransferase," Toxicol. Sci., vol. 144, No. 1, 2015, pp. 163-172.
Zamporlini, et al., "Novel assay for simultaneous measurement of pyridine mononucleotides synthesizing activities allows dissection of the NAD(+) biosynthetic machinery in mammalian cells," FEBS J. Vol. 281, No. 22, 2014, pp. 5104-5119.
Zhao, et al., "Discovery of a Highly Selective NAMPT Inhibitor That Demonstrates Robust Efficacy and Improved Retinal Toxicity with Nicotinic Acid Coadministration," Mol. Cancer Ther., vol. 16, No. 12, 2017, pp. 2677-2688.
Zhou, et al., "Tyrosyl-DNA phosphodiesterase and the repair of 3'-phosphoglycolate-terminated DNA double-strand breaks," DNA Repair, vol. 8, No. 8, 2009, pp. 901-911.

* cited by examiner

| | GSC-0131 | | | GSC-0827 | | |
|---|---|---|---|---|---|---|
| | Rep 1 | Rep 2 | Rep 3 | Rep 1 | Rep 2 | Rep 3 |
| NMRK1 | 25.2 | 25.4 | 11.7 | 0.0 | 0.0 | 0.0 |
| NAMPT | 305.0 | 352.3 | 472.3 | 252.0 | 295.3 | 292.2 |
| TUBB | 2596.0 | 2440.3 | 2178.9 | 2203.5 | 2019.3 | 2096.8 |

| Cancer | R | pval |
|---|---|---|
| NB | -0.532 | 3.80E-36 |
| LGG | -0.405 | 1.40E-20 |
| GB | -0.384 | 1.20E-18 |
| EPD | -0.384 | 2.70E-07 |
| Cell lines | -0.348 | 5.50E-22 |
| Ov | -0.234 | 7.00E-07 |
| Mel | -0.19 | 1.40E-04 |
| AML | n.s | n.s. |
| Bladder | n.s | n.s. |
| Prostate | n.s | n.s. |

| Symbol | logFC | FDR |
|---|---|---|
| *MYC* | 4.86 | 2.92E-183 |
| *CCNB1* | 1.84 | 3.28E-30 |
| *G6PD* | 1.45 | 6.42E-15 |
| *NMRK1* | -2.37 | 2.10E-05 |
| *OSTF1* | -2.39 | 1.59E-29 |

FIG. 7

NMRK1 isoform 1
MKTFIIGISGVTNSGKTTLAKNLQKHLPNCSVISQDDFFKPESEIETDKNGFLQYDVLEA
LNMEKMMSAISCWMESARHSVVSTDQESAEEIPILIIEGFLLFNYKPLDTIWNRSYFLTIP
YEECKRRRSTRVYQPPDSPGYFDGHVWPMYLKYRQEMQDITWEVVYLDGTKSEEDL
FLQVYEDLIQELAKQKCLQVTA (SEQ ID NO: 1)

NMRK1 isoform 2
MKTFIIGISGVTNSGKTTLAKNLQKHLPNCSVISQDDFFKPESEIETDKNGFLQYDVLEA
LNMEKMMSAISCWMESARHSVVSTDQESAEEIPILIIEGFLLFNYNTRVYQPPDSPGYF
DGHVWPMYLKYRQEMQDITWEVVYLDGTKSEEDLFLQVYEDLIQELAKQKCLQVTA
(SEQ ID NO: 2)

NMRK1 isoform 3
MGKRRHRRGNVISCVTNSGKTTLAKNLQKHLPNCSVISQDDFFKPESEIETDKNGFLQ
YDVLEALNMEKMMSAISCWMESARHSVVSTDQESAEEIPILIIEGFLLFNYKPLDTIWNR
SYFLTIPYEECKRRRSTRVYQPPDSPGYFDGHVWPMYLKYRQEMQDITWEVVYLDGT
KSEEDLFLQVYEDLIQELAKQKCLQVTA (SEQ ID NO: 3)

NMRK1 isoform isoform X3
MGKRRHRRGNVISCVTNSGKTTLAKNLQKHLPNCSVISQDDFFKPESEIETDKNGFLQ
YDVLEALNMEKMMSAISCWMESARHSVVSTDQESAEEIPILIIEGFLLFNYNTRVYQPP
DSPGYFDGHVWPMYLKYRQEMQDITWEVVYLDGTKSEEDLFLQVYEDLIQELAKQKC
LQVTA (SEQ ID NO: 4)

NMRK2 isoform 1
MKLIVGIGGMTNGGKTTLTNSLLRALPNCCVIHQDDFFKAPLFQPQDQIAVGEDGFKQ
WDVLESLDMEAMLDTVQAWLSSPQKFARAHGVSVQPEASDTHILLLEGFLLYSYKPLV
DLYSRRYFLTVPYEECKWRRSTRNYTVPDPPGLFDGHVWPMYQKYRQEMEANGVEV
VYLDGMKSREELFREVLEDIQNSLLNRSQESAPSPARPARTQGPGRGCGHRTARPAA
SQQDSM (SEQ ID NO: 5)

NMRK2 isoform 2
MKLIVGIGGMTNGGKTTLTNSLLRALPNCCVIHQDDFFKPQDQIAVGEDGFKQWDVLE
SLDMEAMLDTVQAWLSSPQKFARAHGVSVQPEASDTHILLLEGFLLYSYKPLVDLYSR
RYFLTVPYEECKWRRSTRNYTVPDPPGLFDGHVWPMYQKYRQEMEANGVEVVYLDG
MKSREELFREVLEDIQNSLLNRSQESAPSPARPARTQGPGRGCGHRTARPAASQQDS
M (SEQ ID NO: 6)

FIG. 7 (cont'd)

NMRK2 isoform X1
MKLIVGIGGMTNGGKTTLTNSLLRALPNCCVIHQDDFFKAPLFQPQDQIAVGEDGFKQ
WDVLESLDMEAMLDTVQAWLSSPQKFARAHGVSVQPEASDTHILLLEGFLLYSYNTR
NYTVPDPPGLFDGHVWPMYQKYRQEMEANGVEVVYLDGMKSREELFREVLEDIQNS
LLNRSQESAPSPARPARTQGPGRGCGHRTARPAASQQDSM (SEQ ID NO: 7)

NMRK2 isoform X2
MKLIVGIGGMTNGGKTTLTNSLLRALPNCCVIHQDDFFKPQDQIAVGEDGFKQWDVLE
SLDMEAMLDTVQAWLSSPQKFARAHGVSVQPEASDTHILLLEGFLLYSYNTRNYTVPD
PPGLFDGHVWPMYQKYRQEMEANGVEVVYLDGMKSREELFREVLEDIQNSLLNRSQ
ESAPSPARPARTQGPGRGCGHRTARPAASQQDSM (SEQ ID NO: 8)

NMRK2 isoform X3
MKLIVGIGGMTNGGKTTLTNSLLRALPNCCVIHQDDFFKAPLFQPQDQIAVGEDGFKQ
WDVLESLDMEAMLDTVQAWLSSPQKFARAHGVSVQPEASDTHILLLEGFLLYSYKPLV
DLYSRRYFLTVPYEECKWRRSLPGRHEVPRGALP (SEQ ID NO: 9)

NMRK2 isoform X4
MKLIVGIGGMTNGGKTTLTNSLLRALPNCCVIHQDDFFKPQDQIAVGEDGFKQWDVLE
SLDMEAMLDTVQAWLSSPQKFARAHGVSVQPEASDTHILLLEGFLLYSYKPLVDLYSR
RYFLTVPYEECKWRRSLPGRHEVPRGALP (SEQ ID NO: 10)

myc proto-oncogene protein isoform 1
MDFFRVVENQQPPATMPLNVSFTNRNYDLDYDSVQPYFYCDEEENFYQQQQQSELQ
PPAPSEDIWKKFELLPTPPLSPSRRSGLCSPSYVAVTPFSLRGDNDGGGGSFSTADQL
EMVTELLGGDMVNQSFICDPDDETFIKNIIIQDCMWSGFSAAAKLVSEKLASYQAARKD
SGSPNPARGHSVCSTSSLYLQDLSAAASECIDPSVVFPYPLNDSSSPKSCASQDSSAF
SPSSDSLLSSTESSPQGSPEPLVLHEETPPTTSSDSEEEQEDEEEIDVVSVEKRQAPG
KRSESGSPSAGGHSKPPHSPLVLKRCHVSTHQHNYAAPPSTRKDYPAAKRVKLDSVR
VLRQISNNRKCTSPRSSDTEENVKRRTHNVLERQRRNELKRSFFALRDQIPELENNEK
APKVVILKKATAYILSVQAEEQKLISEEDLLRKRREQLKHKLEQLRNSCA (SEQ ID NO:
11)

myc proto-oncogene protein isoform 2
MDFFRVVENQQPPATMPLNVSFTNRNYDLDYDSVQPYFYCDEEENFYQQQQQSELQP
PAPSEDIWKKFELLPTPPLSPSRRSGLCSPSYVAVTPFSLRGDNDGGGGSFSTADQLE
MVTELLGGDMVNQSFICDPDDETFIKNIIIQDCMWSGFSAAAKLVSEKLASYQAARKDS
GSPNPARGHSVCSTSSLYLQDLSAAASECIDPSVVFPYPLNDSSSPKSCASQDSSAFS
PSSDSLLSSTESSPQGSPEPLVLHEETPPTTSSDSEEEQEDEEEIDVVSVEKRQAPGK
RSESGSPSAGGHSKPPHSPLVLKRCHVSTHQHNYAAPPSTRKDYPAAKRVKLDSVRV
LRQISNNRKCTSPRSSDTEENVKRRTHNVLERQRRNELKRSFFALRDQIPELENNEKA
PKVVILKKATAYILSVQAEEQKLISEEDLLRKRREQLKHKLEQLRNSCA (SEQ ID NO:
12)

SEQUENCE LISTING

```
<160> NUMBER OF SEQ ID NOS: 28

<210> SEQ ID NO 1
<211> LENGTH: 199
<212> TYPE: PRT
<213> ORGANISM: Homo sapiens

<400> SEQUENCE: 1

Met Lys Thr Phe Ile Ile Gly Ile Ser Gly Val Thr Asn Ser Gly Lys
1               5                   10                  15

Thr Thr Leu Ala Lys Asn Leu Gln Lys His Leu Pro Asn Cys Ser Val
            20                  25                  30

Ile Ser Gln Asp Asp Phe Phe Lys Pro Glu Ser Glu Ile Glu Thr Asp
        35                  40                  45

Lys Asn Gly Phe Leu Gln Tyr Asp Val Leu Glu Ala Leu Asn Met Glu
    50                  55                  60

Lys Met Met Ser Ala Ile Ser Cys Trp Met Glu Ser Ala Arg His Ser
65                  70                  75                  80

Val Val Ser Thr Asp Gln Glu Ser Ala Glu Glu Ile Pro Ile Leu Ile
                85                  90                  95

Ile Glu Gly Phe Leu Leu Phe Asn Tyr Lys Pro Leu Asp Thr Ile Trp
            100                 105                 110

Asn Arg Ser Tyr Phe Leu Thr Ile Pro Tyr Glu Glu Cys Lys Arg Arg
        115                 120                 125

Arg Ser Thr Arg Val Tyr Gln Pro Pro Asp Ser Pro Gly Tyr Phe Asp
    130                 135                 140

Gly His Val Trp Pro Met Tyr Leu Lys Tyr Arg Gln Glu Met Gln Asp
145                 150                 155                 160

Ile Thr Trp Glu Val Val Tyr Leu Asp Gly Thr Lys Ser Glu Glu Asp
                165                 170                 175

Leu Phe Leu Gln Val Tyr Glu Asp Leu Ile Gln Glu Leu Ala Lys Gln
            180                 185                 190

Lys Cys Leu Gln Val Thr Ala
        195


<210> SEQ ID NO 2
<211> LENGTH: 175
<212> TYPE: PRT
<213> ORGANISM: Homo sapiens

<400> SEQUENCE: 2

Met Lys Thr Phe Ile Ile Gly Ile Ser Gly Val Thr Asn Ser Gly Lys
1               5                   10                  15
```

-continued

```
Thr Thr Leu Ala Lys Asn Leu Gln Lys His Leu Pro Asn Cys Ser Val
            20                  25                  30

Ile Ser Gln Asp Asp Phe Phe Lys Pro Glu Ser Glu Ile Glu Thr Asp
        35                  40                  45

Lys Asn Gly Phe Leu Gln Tyr Asp Val Leu Glu Ala Leu Asn Met Glu
    50                  55                  60

Lys Met Met Ser Ala Ile Ser Cys Trp Met Glu Ser Ala Arg His Ser
65                  70                  75                  80

Val Val Ser Thr Asp Gln Glu Ser Ala Glu Glu Ile Pro Ile Leu Ile
                85                  90                  95

Ile Glu Gly Phe Leu Leu Phe Asn Tyr Asn Thr Arg Val Tyr Gln Pro
            100                 105                 110

Pro Asp Ser Pro Gly Tyr Phe Asp Gly His Val Trp Pro Met Tyr Leu
        115                 120                 125

Lys Tyr Arg Gln Glu Met Gln Asp Ile Thr Trp Glu Val Val Tyr Leu
    130                 135                 140

Asp Gly Thr Lys Ser Glu Glu Asp Leu Phe Leu Gln Val Tyr Glu Asp
145                 150                 155                 160

Leu Ile Gln Glu Leu Ala Lys Gln Lys Cys Leu Gln Val Thr Ala
                165                 170                 175


<210> SEQ ID NO 3
<211> LENGTH: 203
<212> TYPE: PRT
<213> ORGANISM: Homo sapiens

<400> SEQUENCE: 3

Met Gly Lys Arg Arg His Arg Arg Gly Asn Val Ile Ser Cys Val Thr
1               5                   10                  15

Asn Ser Gly Lys Thr Thr Leu Ala Lys Asn Leu Gln Lys His Leu Pro
            20                  25                  30

Asn Cys Ser Val Ile Ser Gln Asp Asp Phe Phe Lys Pro Glu Ser Glu
        35                  40                  45

Ile Glu Thr Asp Lys Asn Gly Phe Leu Gln Tyr Asp Val Leu Glu Ala
    50                  55                  60

Leu Asn Met Glu Lys Met Met Ser Ala Ile Ser Cys Trp Met Glu Ser
65                  70                  75                  80

Ala Arg His Ser Val Val Ser Thr Asp Gln Glu Ser Ala Glu Glu Ile
                85                  90                  95

Pro Ile Leu Ile Ile Glu Gly Phe Leu Leu Phe Asn Tyr Lys Pro Leu
            100                 105                 110

Asp Thr Ile Trp Asn Arg Ser Tyr Phe Leu Thr Ile Pro Tyr Glu Glu
        115                 120                 125

Cys Lys Arg Arg Arg Ser Thr Arg Val Tyr Gln Pro Pro Asp Ser Pro
    130                 135                 140

Gly Tyr Phe Asp Gly His Val Trp Pro Met Tyr Leu Lys Tyr Arg Gln
145                 150                 155                 160

Glu Met Gln Asp Ile Thr Trp Glu Val Val Tyr Leu Asp Gly Thr Lys
                165                 170                 175

Ser Glu Glu Asp Leu Phe Leu Gln Val Tyr Glu Asp Leu Ile Gln Glu
            180                 185                 190

Leu Ala Lys Gln Lys Cys Leu Gln Val Thr Ala
        195                 200


<210> SEQ ID NO 4
```

-continued

```
<211> LENGTH: 179
<212> TYPE: PRT
<213> ORGANISM: Homo sapiens

<400> SEQUENCE: 4

Met Gly Lys Arg Arg His Arg Arg Gly Asn Val Ile Ser Cys Val Thr
1               5                   10                  15

Asn Ser Gly Lys Thr Thr Leu Ala Lys Asn Leu Gln Lys His Leu Pro
            20                  25                  30

Asn Cys Ser Val Ile Ser Gln Asp Asp Phe Phe Lys Pro Glu Ser Glu
        35                  40                  45

Ile Glu Thr Asp Lys Asn Gly Phe Leu Gln Tyr Asp Val Leu Glu Ala
    50                  55                  60

Leu Asn Met Glu Lys Met Met Ser Ala Ile Ser Cys Trp Met Glu Ser
65                  70                  75                  80

Ala Arg His Ser Val Val Ser Thr Asp Gln Glu Ser Ala Glu Glu Ile
                85                  90                  95

Pro Ile Leu Ile Ile Glu Gly Phe Leu Leu Phe Asn Tyr Asn Thr Arg
            100                 105                 110

Val Tyr Gln Pro Pro Asp Ser Pro Gly Tyr Phe Asp Gly His Val Trp
        115                 120                 125

Pro Met Tyr Leu Lys Tyr Arg Gln Glu Met Gln Asp Ile Thr Trp Glu
    130                 135                 140

Val Val Tyr Leu Asp Gly Thr Lys Ser Glu Glu Asp Leu Phe Leu Gln
145                 150                 155                 160

Val Tyr Glu Asp Leu Ile Gln Glu Leu Ala Lys Gln Lys Cys Leu Gln
                165                 170                 175

Val Thr Ala


<210> SEQ ID NO 5
<211> LENGTH: 235
<212> TYPE: PRT
<213> ORGANISM: Homo sapiens

<400> SEQUENCE: 5

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Ala Pro Leu Phe Gln Pro Gln Asp Gln
        35                  40                  45

Ile Ala Val Gly Glu Asp Gly Phe Lys Gln Trp Asp Val Leu Glu Ser
    50                  55                  60

Leu Asp Met Glu Ala Met Leu Asp Thr Val Gln Ala Trp Leu Ser Ser
65                  70                  75                  80

Pro Gln Lys Phe Ala Arg Ala His Gly Val Ser Val Gln Pro Glu Ala
                85                  90                  95

Ser Asp Thr His Ile Leu Leu Leu Glu Gly Phe Leu Leu Tyr Ser Tyr
            100                 105                 110

Lys Pro Leu Val Asp Leu Tyr Ser Arg Arg Tyr Phe Leu Thr Val Pro
        115                 120                 125

Tyr Glu Glu Cys Lys Trp Arg Arg Ser Thr Arg Asn Tyr Thr Val Pro
    130                 135                 140

Asp Pro Pro Gly Leu Phe Asp Gly His Val Trp Pro Met Tyr Gln Lys
145                 150                 155                 160
```

-continued

```
Tyr Arg Gln Glu Met Glu Ala Asn Gly Val Glu Val Val Tyr Leu Asp
                165                 170                 175

Gly Met Lys Ser Arg Glu Glu Leu Phe Arg Glu Val Leu Glu Asp Ile
            180                 185                 190

Gln Asn Ser Leu Leu Asn Arg Ser Gln Glu Ser Ala Pro Ser Pro Ala
        195                 200                 205

Arg Pro Ala Arg Thr Gln Gly Pro Gly Arg Gly Cys Gly His Arg Thr
    210                 215                 220

Ala Arg Pro Ala Ala Ser Gln Gln Asp Ser Met
225                 230                 235


<210> SEQ ID NO 6
<211> LENGTH: 230
<212> TYPE: PRT
<213> ORGANISM: Homo sapiens

<400> SEQUENCE: 6

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Pro Gln Asp Gln Ile Ala Val Gly Glu
        35                  40                  45

Asp Gly Phe Lys Gln Trp Asp Val Leu Glu Ser Leu Asp Met Glu Ala
    50                  55                  60

Met Leu Asp Thr Val Gln Ala Trp Leu Ser Ser Pro Gln Lys Phe Ala
65                  70                  75                  80

Arg Ala His Gly Val Ser Val Gln Pro Glu Ala Ser Asp Thr His Ile
                85                  90                  95

Leu Leu Leu Glu Gly Phe Leu Leu Tyr Ser Tyr Lys Pro Leu Val Asp
            100                 105                 110

Leu Tyr Ser Arg Arg Tyr Phe Leu Thr Val Pro Tyr Glu Glu Cys Lys
        115                 120                 125

Trp Arg Arg Ser Thr Arg Asn Tyr Thr Val Pro Asp Pro Pro Gly Leu
    130                 135                 140

Phe Asp Gly His Val Trp Pro Met Tyr Gln Lys Tyr Arg Gln Glu Met
145                 150                 155                 160

Glu Ala Asn Gly Val Glu Val Val Tyr Leu Asp Gly Met Lys Ser Arg
                165                 170                 175

Glu Glu Leu Phe Arg Glu Val Leu Glu Asp Ile Gln Asn Ser Leu Leu
            180                 185                 190

Asn Arg Ser Gln Glu Ser Ala Pro Ser Pro Ala Arg Pro Ala Arg Thr
        195                 200                 205

Gln Gly Pro Gly Arg Gly Cys Gly His Arg Thr Ala Arg Pro Ala Ala
    210                 215                 220

Ser Gln Gln Asp Ser Met
225                 230


<210> SEQ ID NO 7
<211> LENGTH: 211
<212> TYPE: PRT
<213> ORGANISM: Homo sapiens

<400> SEQUENCE: 7

Met Lys Leu Ile Val Gly Ile Gly Gly Met Thr Asn Gly Gly Lys Thr
1               5                   10                  15
```

```
Thr Leu Thr Asn Ser Leu Leu Arg Ala Leu Pro Asn Cys Cys Val Ile
            20                  25                  30

His Gln Asp Asp Phe Phe Lys Ala Pro Leu Phe Gln Pro Gln Asp Gln
        35                  40                  45

Ile Ala Val Gly Glu Asp Gly Phe Lys Gln Trp Asp Val Leu Glu Ser
    50                  55                  60

Leu Asp Met Glu Ala Met Leu Asp Thr Val Gln Ala Trp Leu Ser Ser
65                  70                  75                  80

Pro Gln Lys Phe Ala Arg Ala His Gly Val Ser Val Gln Pro Glu Ala
                85                  90                  95

Ser Asp Thr His Ile Leu Leu Leu Glu Gly Phe Leu Leu Tyr Ser Tyr
            100                 105                 110

Asn Thr Arg Asn Tyr Thr Val Pro Asp Pro Pro Gly Leu Phe Asp Gly
        115                 120                 125

His Val Trp Pro Met Tyr Gln Lys Tyr Arg Gln Glu Met Glu Ala Asn
    130                 135                 140

Gly Val Glu Val Val Tyr Leu Asp Gly Met Lys Ser Arg Glu Glu Leu
145                 150                 155                 160

Phe Arg Glu Val Leu Glu Asp Ile Gln Asn Ser Leu Leu Asn Arg Ser
                165                 170                 175

Gln Glu Ser Ala Pro Ser Pro Ala Arg Pro Ala Arg Thr Gln Gly Pro
            180                 185                 190

Gly Arg Gly Cys Gly His Arg Thr Ala Arg Pro Ala Ala Ser Gln Gln
        195                 200                 205

Asp Ser Met
    210


<210> SEQ ID NO 8
<211> LENGTH: 206
<212> TYPE: PRT
<213> ORGANISM: Homo sapiens

<400> SEQUENCE: 8

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Pro Gln Asp Gln Ile Ala Val Gly Glu
        35                  40                  45

Asp Gly Phe Lys Gln Trp Asp Val Leu Glu Ser Leu Asp Met Glu Ala
    50                  55                  60

Met Leu Asp Thr Val Gln Ala Trp Leu Ser Ser Pro Gln Lys Phe Ala
65                  70                  75                  80

Arg Ala His Gly Val Ser Val Gln Pro Glu Ala Ser Asp Thr His Ile
                85                  90                  95

Leu Leu Leu Glu Gly Phe Leu Leu Tyr Ser Tyr Asn Thr Arg Asn Tyr
            100                 105                 110

Thr Val Pro Asp Pro Pro Gly Leu Phe Asp Gly His Val Trp Pro Met
        115                 120                 125

Tyr Gln Lys Tyr Arg Gln Glu Met Glu Ala Asn Gly Val Glu Val Val
    130                 135                 140

Tyr Leu Asp Gly Met Lys Ser Arg Glu Glu Leu Phe Arg Glu Val Leu
145                 150                 155                 160

Glu Asp Ile Gln Asn Ser Leu Leu Asn Arg Ser Gln Glu Ser Ala Pro
                165                 170                 175
```

```
Ser Pro Ala Arg Pro Ala Arg Thr Gln Gly Pro Gly Arg Gly Cys Gly
            180                 185                 190

His Arg Thr Ala Arg Pro Ala Ala Ser Gln Gln Asp Ser Met
        195                 200                 205


<210> SEQ ID NO 9
<211> LENGTH: 150
<212> TYPE: PRT
<213> ORGANISM: Homo sapiens

<400> SEQUENCE: 9

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Ala Pro Leu Phe Gln Pro Gln Asp Gln
        35                  40                  45

Ile Ala Val Gly Glu Asp Gly Phe Lys Gln Trp Asp Val Leu Glu Ser
    50                  55                  60

Leu Asp Met Glu Ala Met Leu Asp Thr Val Gln Ala Trp Leu Ser Ser
65                  70                  75                  80

Pro Gln Lys Phe Ala Arg Ala His Gly Val Ser Val Gln Pro Glu Ala
                85                  90                  95

Ser Asp Thr His Ile Leu Leu Leu Glu Gly Phe Leu Leu Tyr Ser Tyr
            100                 105                 110

Lys Pro Leu Val Asp Leu Tyr Ser Arg Arg Tyr Phe Leu Thr Val Pro
        115                 120                 125

Tyr Glu Glu Cys Lys Trp Arg Arg Ser Leu Pro Gly Arg His Glu Val
    130                 135                 140

Pro Arg Gly Ala Leu Pro
145                 150


<210> SEQ ID NO 10
<211> LENGTH: 145
<212> TYPE: PRT
<213> ORGANISM: Homo sapiens

<400> SEQUENCE: 10

Met Lys Leu Ile Val Gly Ile Gly Gly Met Thr Asn Gly Gly Lys Thr
1               5                   10                  15

Thr Leu Thr Asn Ser Leu Leu Arg Ala Leu Pro Asn Cys Cys Val Ile
            20                  25                  30

His Gln Asp Asp Phe Phe Lys Pro Gln Asp Gln Ile Ala Val Gly Glu
        35                  40                  45

Asp Gly Phe Lys Gln Trp Asp Val Leu Glu Ser Leu Asp Met Glu Ala
    50                  55                  60

Met Leu Asp Thr Val Gln Ala Trp Leu Ser Ser Pro Gln Lys Phe Ala
65                  70                  75                  80

Arg Ala His Gly Val Ser Val Gln Pro Glu Ala Ser Asp Thr His Ile
                85                  90                  95

Leu Leu Leu Glu Gly Phe Leu Leu Tyr Ser Tyr Lys Pro Leu Val Asp
            100                 105                 110

Leu Tyr Ser Arg Arg Tyr Phe Leu Thr Val Pro Tyr Glu Glu Cys Lys
        115                 120                 125

Trp Arg Arg Ser Leu Pro Gly Arg His Glu Val Pro Arg Gly Ala Leu
    130                 135                 140
```

Pro
145

<210> SEQ ID NO 11
<211> LENGTH: 454
<212> TYPE: PRT
<213> ORGANISM: Homo sapiens

<400> SEQUENCE: 11

Met Asp Phe Phe Arg Val Val Glu Asn Gln Gln Pro Pro Ala Thr Met
1 5 10 15

Pro Leu Asn Val Ser Phe Thr Asn Arg Asn Tyr Asp Leu Asp Tyr Asp
20 25 30

Ser Val Gln Pro Tyr Phe Tyr Cys Asp Glu Glu Glu Asn Phe Tyr Gln
35 40 45

Gln Gln Gln Gln Ser Glu Leu Gln Pro Pro Ala Pro Ser Glu Asp Ile
50 55 60

Trp Lys Lys Phe Glu Leu Leu Pro Thr Pro Pro Leu Ser Pro Ser Arg
65 70 75 80

Arg Ser Gly Leu Cys Ser Pro Ser Tyr Val Ala Val Thr Pro Phe Ser
85 90 95

Leu Arg Gly Asp Asn Asp Gly Gly Gly Gly Ser Phe Ser Thr Ala Asp
100 105 110

Gln Leu Glu Met Val Thr Glu Leu Leu Gly Gly Asp Met Val Asn Gln
115 120 125

Ser Phe Ile Cys Asp Pro Asp Asp Glu Thr Phe Ile Lys Asn Ile Ile
130 135 140

Ile Gln Asp Cys Met Trp Ser Gly Phe Ser Ala Ala Ala Lys Leu Val
145 150 155 160

Ser Glu Lys Leu Ala Ser Tyr Gln Ala Ala Arg Lys Asp Ser Gly Ser
165 170 175

Pro Asn Pro Ala Arg Gly His Ser Val Cys Ser Thr Ser Ser Leu Tyr
180 185 190

Leu Gln Asp Leu Ser Ala Ala Ala Ser Glu Cys Ile Asp Pro Ser Val
195 200 205

Val Phe Pro Tyr Pro Leu Asn Asp Ser Ser Ser Pro Lys Ser Cys Ala
210 215 220

Ser Gln Asp Ser Ser Ala Phe Ser Pro Ser Ser Asp Ser Leu Leu Ser
225 230 235 240

Ser Thr Glu Ser Ser Pro Gln Gly Ser Pro Glu Pro Leu Val Leu His
245 250 255

Glu Glu Thr Pro Pro Thr Thr Ser Ser Asp Ser Glu Glu Glu Gln Glu
260 265 270

Asp Glu Glu Glu Ile Asp Val Val Ser Val Glu Lys Arg Gln Ala Pro
275 280 285

Gly Lys Arg Ser Glu Ser Gly Ser Pro Ser Ala Gly Gly His Ser Lys
290 295 300

Pro Pro His Ser Pro Leu Val Leu Lys Arg Cys His Val Ser Thr His
305 310 315 320

Gln His Asn Tyr Ala Ala Pro Pro Ser Thr Arg Lys Asp Tyr Pro Ala
325 330 335

Ala Lys Arg Val Lys Leu Asp Ser Val Arg Val Leu Arg Gln Ile Ser
340 345 350

Asn Asn Arg Lys Cys Thr Ser Pro Arg Ser Ser Asp Thr Glu Glu Asn

-continued

```
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450


<210> SEQ ID NO 12
<211> LENGTH: 453
<212> TYPE: PRT
<213> ORGANISM: Homo sapiens

<400> SEQUENCE: 12

Met Asp Phe Phe Arg Val Val Glu Asn Gln Pro Pro Ala Thr Met Pro
1               5                   10                  15

Leu Asn Val Ser Phe Thr Asn Arg Asn Tyr Asp Leu Asp Tyr Asp Ser
            20                  25                  30

Val Gln Pro Tyr Phe Tyr Cys Asp Glu Glu Glu Asn Phe Tyr Gln Gln
        35                  40                  45

Gln Gln Gln Ser Glu Leu Gln Pro Pro Ala Pro Ser Glu Asp Ile Trp
    50                  55                  60

Lys Lys Phe Glu Leu Leu Pro Thr Pro Pro Leu Ser Pro Ser Arg Arg
65                  70                  75                  80

Ser Gly Leu Cys Ser Pro Ser Tyr Val Ala Val Thr Pro Phe Ser Leu
                85                  90                  95

Arg Gly Asp Asn Asp Gly Gly Gly Gly Ser Phe Ser Thr Ala Asp Gln
            100                 105                 110

Leu Glu Met Val Thr Glu Leu Leu Gly Gly Asp Met Val Asn Gln Ser
        115                 120                 125

Phe Ile Cys Asp Pro Asp Asp Glu Thr Phe Ile Lys Asn Ile Ile Ile
    130                 135                 140

Gln Asp Cys Met Trp Ser Gly Phe Ser Ala Ala Ala Lys Leu Val Ser
145                 150                 155                 160

Glu Lys Leu Ala Ser Tyr Gln Ala Ala Arg Lys Asp Ser Gly Ser Pro
                165                 170                 175

Asn Pro Ala Arg Gly His Ser Val Cys Ser Thr Ser Ser Leu Tyr Leu
            180                 185                 190

Gln Asp Leu Ser Ala Ala Ala Ser Glu Cys Ile Asp Pro Ser Val Val
        195                 200                 205

Phe Pro Tyr Pro Leu Asn Asp Ser Ser Ser Pro Lys Ser Cys Ala Ser
    210                 215                 220

Gln Asp Ser Ser Ala Phe Ser Pro Ser Ser Asp Ser Leu Leu Ser Ser
225                 230                 235                 240

Thr Glu Ser Ser Pro Gln Gly Ser Pro Glu Pro Leu Val Leu His Glu
                245                 250                 255

Glu Thr Pro Pro Thr Thr Ser Ser Asp Ser Glu Glu Glu Gln Glu Asp
            260                 265                 270
```

-continued

```
Glu Glu Glu Ile Asp Val Val Ser Val Glu Lys Arg Gln Ala Pro Gly
        275                 280                 285

Lys Arg Ser Glu Ser Gly Ser Pro Ser Ala Gly Gly His Ser Lys Pro
    290                 295                 300

Pro His Ser Pro Leu Val Leu Lys Arg Cys His Val Ser Thr His Gln
305                 310                 315                 320

His Asn Tyr Ala Ala Pro Pro Ser Thr Arg Lys Asp Tyr Pro Ala Ala
                325                 330                 335

Lys Arg Val Lys Leu Asp Ser Val Arg Val Leu Arg Gln Ile Ser Asn
            340                 345                 350

Asn Arg Lys Cys Thr Ser Pro Arg Ser Ser Asp Thr Glu Glu Asn Val
        355                 360                 365

Lys Arg Arg Thr His Asn Val Leu Glu Arg Gln Arg Arg Asn Glu Leu
    370                 375                 380

Lys Arg Ser Phe Phe Ala Leu Arg Asp Gln Ile Pro Glu Leu Glu Asn
385                 390                 395                 400

Asn Glu Lys Ala Pro Lys Val Val Ile Leu Lys Lys Ala Thr Ala Tyr
                405                 410                 415

Ile Leu Ser Val Gln Ala Glu Glu Gln Lys Leu Ile Ser Glu Glu Asp
            420                 425                 430

Leu Leu Arg Lys Arg Arg Glu Gln Leu Lys His Lys Leu Glu Gln Leu
        435                 440                 445

Arg Asn Ser Cys Ala
    450


<210> SEQ ID NO 13
<211> LENGTH: 24
<212> TYPE: DNA
<213> ORGANISM: Artificial Sequence
<220> FEATURE:
<223> OTHER INFORMATION: forward primer to detect NMRK

<400> SEQUENCE: 13

ccaaattgca gtgtcatatc tcag                                              24


<210> SEQ ID NO 14
<211> LENGTH: 22
<212> TYPE: DNA
<213> ORGANISM: Artificial Sequence
<220> FEATURE:
<223> OTHER INFORMATION: reverse primer to detect NMRK

<400> SEQUENCE: 14

ccagcaggaa atggctgaca tc                                                22


<210> SEQ ID NO 15
<211> LENGTH: 23
<212> TYPE: DNA
<213> ORGANISM: Artificial Sequence
<220> FEATURE:
<223> OTHER INFORMATION: forward primer to detect NMRK2

<400> SEQUENCE: 15

ccatgtacca gaagtatagg cag                                               23


<210> SEQ ID NO 16
<211> LENGTH: 23
<212> TYPE: DNA
<213> ORGANISM: Artificial Sequence
<220> FEATURE:
<223> OTHER INFORMATION: reverse primer to detect NMRK2
```

<400> SEQUENCE: 16
gcgagttctg aatgtcttcc agg 23

<210> SEQ ID NO 17
<211> LENGTH: 21
<212> TYPE: DNA
<213> ORGANISM: Artificial Sequence
<220> FEATURE:
<223> OTHER INFORMATION: forward primer for MYC

<400> SEQUENCE: 17
cctggtgctc catgaggaga c 21

<210> SEQ ID NO 18
<211> LENGTH: 22
<212> TYPE: DNA
<213> ORGANISM: Artificial Sequence
<220> FEATURE:
<223> OTHER INFORMATION: reverse primer for MYC

<400> SEQUENCE: 18
cagactctga ccttttgcca gg 22

<210> SEQ ID NO 19
<211> LENGTH: 22
<212> TYPE: DNA
<213> ORGANISM: Artificial Sequence
<220> FEATURE:
<223> OTHER INFORMATION: forward primer for MYCN

<400> SEQUENCE: 19
accacaaggc cctcagtacc tc 22

<210> SEQ ID NO 20
<211> LENGTH: 22
<212> TYPE: DNA
<213> ORGANISM: Artificial Sequence
<220> FEATURE:
<223> OTHER INFORMATION: reverse primer for MYCN

<400> SEQUENCE: 20
tgacagcctt ggtgttggag ga 22

<210> SEQ ID NO 21
<211> LENGTH: 20
<212> TYPE: RNA
<213> ORGANISM: Artificial Sequence
<220> FEATURE:
<223> OTHER INFORMATION: Sg Guide 1

<400> SEQUENCE: 21
ucuugcgcuu uccauccagc 20

<210> SEQ ID NO 22
<211> LENGTH: 20
<212> TYPE: RNA
<213> ORGANISM: Artificial Sequence
<220> FEATURE:
<223> OTHER INFORMATION: Sg Guide 2

<400> SEQUENCE: 22
agugcuugaa gcacuuaaca 20

<210> SEQ ID NO 23

<211> LENGTH: 20
<212> TYPE: RNA
<213> ORGANISM: Artificial Sequence
<220> FEATURE:
<223> OTHER INFORMATION: Sg Guide 3

<400> SEQUENCE: 23
ugaugucagc cauuuccugc 20

<210> SEQ ID NO 24
<211> LENGTH: 24
<212> TYPE: DNA
<213> ORGANISM: Artificial Sequence
<220> FEATURE:
<223> OTHER INFORMATION: NMRK1 Nucleofectin forward sequencing primer

<400> SEQUENCE: 24
aaaaatgttt cactgtggtt tgtc 24

<210> SEQ ID NO 25
<211> LENGTH: 20
<212> TYPE: DNA
<213> ORGANISM: Artificial Sequence
<220> FEATURE:
<223> OTHER INFORMATION: NMRK1 Nucleofectin forward sequencing primer

<400> SEQUENCE: 25
agagtgtctt gcgctttcca 20

<210> SEQ ID NO 26
<211> LENGTH: 24
<212> TYPE: DNA
<213> ORGANISM: Artificial Sequence
<220> FEATURE:
<223> OTHER INFORMATION: NMRK1 Nucleofectin reverse sequencing primer

<400> SEQUENCE: 26
actgtggttt gtcagcatta gagt 24

<210> SEQ ID NO 27
<211> LENGTH: 21
<212> TYPE: DNA
<213> ORGANISM: Artificial Sequence
<220> FEATURE:
<223> OTHER INFORMATION: NMRK1 Nucleofectin reverse sequencing primer

<400> SEQUENCE: 27
cagcaggaaa tggctgacat c 21

<210> SEQ ID NO 28
<211> LENGTH: 689
<212> TYPE: DNA
<213> ORGANISM: Artificial Sequence
<220> FEATURE:
<223> OTHER INFORMATION: NMRK1 synthesized as g-block

<400> SEQUENCE: 28
cgggatcaac aagtttgtac aaaaaagttg gcatgaaaac atttatcatt ggaatcagtg 60
gtgtgacaaa cagtggcaaa acaacactgg ctaagaattt gcagaaacac ctcccaaatt 120
gcagtgtcat atctcaggat gatttcttca agccagagtc tgagatagag acagataaaa 180
atggattttt gcagtacgat gtgcttgaag cacttaacat ggaaaaaatg atgtcagcca 240
tttcctgctg gatggaaagc gcaagacact ctgtggtatc aacagaccag gaaagtgctg 300
aggaaattcc cattttaatc atcgaaggtt ttcttctttt taattataag ccccttgaca 360

-continued

```
ctatatggaa tagaagctat ttcctgacga ttccatatga agaatgtaaa aggaggagga    420

gtacaagggt ctatcagcct ccagactctc cgggatactt tgatggccat gtgtggccca    480

tgtatctaaa gtacagacaa gaaatgcagg acatcacatg ggaagttgtg tacctggatg    540

gaacaaaatc tgaagaggac ctctttttgc aagtatatga agatctaata caagaactag    600

caaagcaaaa gtgtttgcaa gtgacagcat aacaaaaccc aagtcaccat gtacttgccc    660

aactttcttg tacaaagtgg ttggtaagc                                      689
```

CANCER COMBINATION THERAPIES UTILIZING A NICOTINAMIDE PHOSPHORIBOSYLTRANSFERASE INHIBITOR IN COMBINATION WITH A NICOTINAMIDE ADENINE DINUCLEOTIDE SALVAGE PATHWAY PRECURSOR

CROSS-REFERENCE TO RELATED APPLICATIONS

This application is a US National Phase Application based on International Patent Application No. PCT/US2020/024019 filed Mar. 20, 2020, which claims priority to U.S. Provisional Patent Application No. 62/821,821 filed Mar. 21, 2019, both of which are incorporated by reference herein as if fully set forth herein.

REFERENCE TO SEQUENCE LISTING

The Sequence Listing associated with this application is provided in text format in lieu of a paper copy and is hereby incorporated by reference into the specification. The name of the text file containing the Sequence Listing is 2K28619_ST25.txt. The text file is 28.8 KB, was created on Sep. 16, 2021 and is being submitted electronically via EFS-Web.

STATEMENT REGARDING FEDERALLY SPONSORED RESEARCH OR DEVELOPMENT

This invention was made with government support under CA190957 and CA015704 awarded by the National Institutes of Health. The government has certain rights in the invention.

FIELD OF THE DISCLOSURE

The current disclosure provides cancer combination therapies utilizing a nicotinamide phosphoribosyltransferase (NAMPT) inhibitor in combination with a nicotinamide adenine dinucleotide (NAD) salvage pathway precursor. Cancers treated with the combination therapies can be nicotinamide riboside kinase (NMRK) low cancers and/or Myc high cancers and can include various forms of glioblastomas, among other cancer types.

BACKGROUND OF THE DISCLOSURE

Alterations in cell metabolism have emerged as one of the hallmarks of cancer that could provide avenues to selectively target cancerous cells with therapeutic interventions. For example, cancer cells seem to require higher levels of nicotinamide adenine dinucleotide (NAD) than non-cancerous cells. NAD acts both as a co-enzyme in cellular redox reactions and as a substrate for enzymes. Cellular metabolism of NAD also appears to have a crucial role in the fate of cancer cells. Thus, one approach to targeting cancer cells has been to inhibit cellular NAD biosynthesis pathways.

The enzyme nicotinamide phosphoribosyltransferase (NAMPT) plays a key role in the biosynthesis of NAD in mammalian cells. It is the rate-limiting enzyme that catalyzes the first reaction of the synthesis of NAD from nicotinamide. Further, mounting evidence indicates that NAMPT is also frequently up-regulated in both solid and hematologic cancers. Based on NAMPT's upregulation and role in NAD biosynthesis, attempts have been made to treat cancers based on NAMPT inhibition.

In preclinical studies, NAMPT inhibition resulted in remarkable anticancer activity. However, clinical results based on NAMPT inhibition to date have been disappointing. First, administration of NAMPT inhibitors can be associated with significant dose-limiting toxicities. Further, the less than hoped-for efficacy may be due to other alternative pathways for NAD biosynthesis in cells. In particular, NAD biosynthesis can be mediated by de novo biosynthesis of NAD from tryptophan (the nicotinic acid dependent pathway) as well as through other salvage pathways, in particular, one that relies on external factors, such as vitamins, to produce NAD+.

SUMMARY OF THE DISCLOSURE

The current disclosure provides treating sub-types of cancers with nicotinamide phosphoribosyltransferase (NAMPT) inhibitors in combination with a nicotinamide adenine dinucleotide (NAD) salvage pathway external factor. This strategy is based on the insight that normal, non-cancerous cells can survive NAMPT inhibition by utilizing an external factor that allows NAD production through a salvage pathway. However, a subset of cancer cells are not able to survive NAM PT inhibition in the presence of the external factor because the NAD salvage pathway has become unavailable in these cells. Thus, NAMPT inhibitors can be administered in combination with an external factor that restores NAD synthesis through an alternative pathway in normal cells but not in cancerous cells. This strategy results in selective killing of cancer cells and increases the therapeutic index of NAD synthesis inhibitors, such as NAMPT inhibitors.

In particular embodiments, NAMPT inhibitors administered as part of the combination therapies disclosed herein include FK866 ((E)-N-[4-(1-benzoyl-4-yl)-butyl]-3-(pyridin-3-yl) acrylamide), CHS-828 (N-[6-(4-chlorophenoxy) hexyl]-N'-cyano-N"-4-pyridinyl-guanidine (also referred to as GMX1778), GNE-617 (N-(4-((3,5-difluorophenyl)sulfonyl)-benzypimidazo[1,2-a]pyridine-6-carboxamide), GNE-618 (N-[[4-[[3-(Trifluoromethyl)phenyl]sulfonyl] phenyl] methyl]-1H-pyrazolo[3,4-b]pyridine-5-carboxamide), STF118804 (4-[5-Methyl-4-[[(4-methyl-phenyl]sulfonyl] methyl]-2-oxazolyl]-N-(3-pyridinylmethyl)benzamide), KPT-9274 ((E)-3-(6-amino-pyridin-3-yl)-N-[[5-[4-(4,4-difluoropiperidine-1-carbon)phenyl]-7-(4-fluorophenyl)-1-benzofuran-2-yl] methyl]prop-2-enamide), and/or LSN3154567 (2-hydroxy-2-methyl-N-[1,2,3,4-tetrahydro-2-[2-(3-pyridinyloxy)acetyl]-6-isoquinolinyl]-1-propanesulfonamide. In particular embodiments, external factors include nicotinamide mononucleotide (NMN) and/or nicotinamide riboside (NR).

In particular embodiments, cancers that are susceptible to the combination therapies described herein are nicotinamide riboside kinase $(NRMK1)^{low}$ cancers and/or $MYC^{hi}$ cancers. The cancer subtypes can also include $MYC/MYCN^{hi}$ cancers. In particular embodiments, the $NRMK1^{low}$ and/or $MYC/MYCN^{hi}$ cancers include neuroblastomas, low grade gliomas, glioblastomas, and ependymomas.

BRIEF DESCRIPTION OF THE SEVERAL VIEWS OF THE DRAWINGS

Many of the drawings submitted herein are better understood in color. Applicant considers the color versions of the drawings as part of the original submission and reserve the right to present color images of the drawings in later proceedings.

FIG. 7. Exemplary sequences supporting the disclosure (SEQ ID NOs. 1-12).

DETAILED DESCRIPTION

Figure 1:
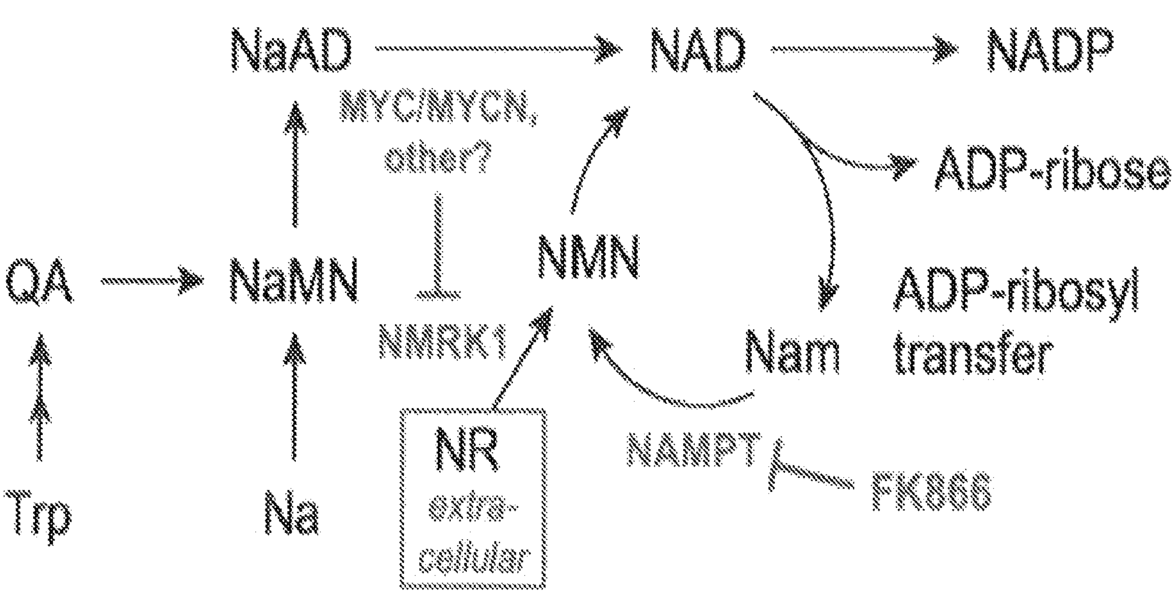
FIG. 1. NAD biosynthesis and salvage pathways. NAD is a co-substrate involved in multiple enzymatic reactions, involving redox, deacetylation, mono- and poly (ADP-ribose) polymerization, and cyclic ADP-ribose synthesis. Although NAD can be synthesized de novo from tryptophan, NAD consumption in non-redox reactions necessitates salvage pathways, most prominently, re-utilization of intracellular nicotinamide by NAMPT. However, there is also an extracellular salvage pathway whereby the NAD precursor nicotinamide riboside (NR) can be up taken by cells and shuttled into the pathway via phosphorylation by nicotinamide riboside kinase (NMRK1).

Alterations in cell metabolism have emerged as one of the hallmarks of cancer that could provide avenues to selectively target cancerous cells with therapeutic interventions. For example, cancer cells seem to require higher levels of nicotinamide adenine dinucleotide (NAD) than non-cancerous cells.

The role of NAD in cellular respiration is well understood. As glucose and fatty acids are oxidized, NAD can accept a hydride equivalent, which results in its reduction to NADH. NADH can donate a hydride equivalent, resulting in oxidation back to NAD. These reduction-oxidation cycles use NAD for the temporary storage of hydride ion, but they do not consume NAD.

Poly-ADPribose polymerases (PARPs), ADPribose transferases (ARTs), and SIRTs all catalyze reactions that release nicotinamide from NAD. These reactions generate a significant amount of energy, similar to ATP hydrolysis. The reverse reaction does not occur readily, so NAD must be replenished by other mechanisms (Bogan & Brenner, Annu. Rev. Nutr. 2008, 28, 115-130).

Cellular metabolism of NAD also appears to have a crucial role in the fate of cancer cells. Thus, one approach to targeting cancer cells has been to inhibit cellular NAD biosynthesis pathways.

The enzyme nicotinamide phosphoribosyltransferase (NAMPT) plays a key role in the biosynthesis of NAD in mammalian cells. NAMPT was originally identified as a gene product expressed in activated peripheral human lymphocytes and was implicated in the maturation of B cell precursors, and hence was named pre-B cell enhancing factor. Subsequent studies revealed that NAMPT is upregulated during neutrophil activation and acts as an antiapoptotic factor for neutrophils in clinical and experimental sepsis. Increased NAMPT levels are observed in stimulated monocytes and during all-trans-retinoid acid (ATRA) induced granulocytic differentiation of the myeloid leukemia cell line HL-60. The cytokines interleukin-1p (IL-1p), tumor necrosis factor and IL-6 induce NAMPT expression.

NAMPT converts nicotinamide to nicotinamide mononucleotide (NMN), which is converted into NAD by nicotinamide mononucleotide adenylyltransferase in the mammalian biosynthetic pathway. NAMPT is the rate-limiting factor in NAD salvage biosynthesis from nicotinamide. Further, mounting evidence indicates that NAMPT is also frequently up-regulated in both solid and hematologic cancers. Based on NAMPT's upregulation and role in NAD biosynthesis, attempts have been made to treat cancers based on NAMPT inhibition.

In preclinical studies, NAMPT inhibition resulted in remarkable anticancer activity. However, clinical results based on NAMPT inhibition to date have been disappointing. First, administration of NAMPT inhibitors can be associated with significant dose-limiting toxicities. Further, the less than hoped-for efficacy may be due to other alternative pathways for NAD biosynthesis in cells. In particular, NAD biosynthesis can be mediated by de novo biosynthesis of NAD from tryptophan (the nicotinic acid dependent pathway) and other salvage pathways, in particular, one that relies on external factors, such as vitamins, to produce NAD.

The current disclosure provides treating sub-types of cancers with nicotinamide phosphoribosyltransferase (NAMPT) inhibitors in combination with a nicotinamide adenine dinucleotide (NAD) salvage pathway external factor. This strategy is based on the insight that normal, non-cancerous cells can survive NAMPT inhibition by utilizing an external factor that allows NAD production through a salvage pathway. However, a subset of cancer cells are not able to survive NAM PT inhibition in the presence of the external factor because the NAD salvage pathway has become unavailable in these cells. Thus, NAMPT inhibitors can be administered in combination with an external factor that restores NAD synthesis through an alternative pathway that is only available in non-cancerous cells. This strategy results in selective killing of cancer cells and increases the therapeutic index of NAD synthesis inhibitors, such as NAM PT inhibitors.

The described combination therapies were developed in part based on metabolic enzyme inhibitor screens in patient glioblastoma (GBM) stem-like cells (GSCs), where a subset of brain tumor cells with exquisite sensitivity to NAMPT inhibitors, such as FK866, in the presence of extracellular NAD precursors were identified.

In particular embodiments, cancers that are susceptible to the combination therapies described herein are nicotinamide riboside kinase $(NRMK1)^{low}$ cancers and/or $MYC^{hi}$ cancers. The cancer subtypes can also include $MYC/MYCN^{hi}$ cancers. These sub-types of cancers are prioritized because in experimental work, it was noted that cells more susceptible to this combination (i.e., NAMPT inhibitor+NMN or NR) exhibit loss of expression of NMRK1, an enzyme in a parallel NAD salvage pathway utilizing exogenous nicotinamide riboside (NR; FIG. 1). In follow up studies, it was found that loss of expression of NMRK1, part of the NAD salvage pathway, confers this sensitivity in GBM and atypical teratoid rhabdoid tumors (ATRT) patient-derived cell lines. Importantly, NMRK1 is expressed in normal organs/tissues surveyed by the ENCODE project (e.g., blood, brain, epithelium, heart, intestine, kidney, muscle, etc.), indicating safety of normal tissues in practice of the combination therapies.

Particular embodiments include integrating $NMKR1^{low}$ status with other clinically relevant features indicating standard of care for a particular subject. For example, for GBM, in addition to correlating with MYC and MYCN expression, $NMRK1^{low}$ expression status is also significantly associated with OLIG2 expression (p=3e-24), a key classifier of the proneural GBM subtype. This subtype represents almost ⅓ of GBM. For neuroblastoma, NMKR1 and PD-L1/CD274 expression are positively correlated in a (Rval=0.53, p=8e-37). Thus, therapies described herein could be particularly well suited for PD-L1 therapy resistant tumors.

In particular embodiments, NAMPT inhibitors used in the combination therapies disclosed herein include FK866 ((E)-N-[4-(1-benzoyl-4-yl)-butyl]-3-(pyridin-3-yl) acrylamide), CHS-828 (N-[6-(4-chlorophenoxy)hexyl]-N'-cyano-N"-4-pyridinyl-guanidine (also referred to as GMX1778), GNE-617 (N-(4-((3,5-difluorophenyl)sulfonyl)benzypimidazo[1,2-a]pyridine-6-carboxamide), GNE-618 (N-[[4-[[3-(Trifluoromethyl)phenyl]sulfonyl]phenyl]methyl]-1H-pyrazolo[3,4-b]pyridine-5-carboxamide), STF118804 (4-[5-Methyl-4-[[(4-methylphenyl)sulfonyl]methyl]-2-oxazolyl]-N-(3-pyridinylmethyl) benzamide), KPT-9274 ((E)-3-(6-aminopyridin-3-yl)-N-[[5-[4-(4,4-diiodopiperidine-1-carbonyl)phenyl]-7-(4-fluorophenyl)-1-benzofuran-2-yl] methyl]prop-2-enamide), and/or LSN3154567 (2-hydroxy-2-methyl-N-[1,2,3,4-tetrahydro-2-[2-(3-pyridinyloxy) acetyl]-6-isoquinolinyl]-1-propane-sulfonamide.

For more information regarding GNE-618 and GNE-617, see WO2017162840; Olesen et al., Biochem Biophys Res Commun 2008; 367:799-804; and Beauparlant et al., Anti-cancer Drugs. 2009 June. 20(5):346-54). For more information regarding STF118804, see Sampath et al., Pharmacology & Therapeutics (2014), http://dx.doi.org/10.1016/j.pharmthera. 2015.02.004. For more information regarding KPT-9274, see Rane et al., Nature Scientific Reports, 7:42555 (DOI:10.1038/srep42555; Karyopharm Therapeutics; under Phase I development for the treatment of advanced solid malignancies including sarcoma, colon cancer, lung cancer, triple negative breast cancer, renal cell carcinoma, acute myeloid leukemia and non-Hodgkin's lymphoma). For more information regarding LSN3154567, see Zhao et al., DOI: 10.1158/1535-7163.MCT-16-0674).

In particular embodiments, external factors include NMN and/or NR.

Aspects of the disclosure are now described in additional detail as follows: (i) $NMRK^{low}$ and/or $Myc^{high}$ Cancers, (ii) NAMPT and NAMPT Inhibitors, (iii) External Factors, (iv) Compositions for Administration, (v) Methods of Use, (vi) Kits, (vii) Screening Tools, (viii) Exemplary Embodiments, and (ix) Experimental Examples.

$NMRK^{low}$ and/or $Myc^{high}$ Cancers. The combination therapies disclosed herein are useful to treat $NMRK^{low}$ and/or $Myc^{high}$ cancers. NMRK1 is an enzyme in a parallel NAD salvage pathway utilizing exogenous NR. In particular embodiments, an NMRK protein is an enzyme capable of phosphorylating NR. See FIG. 7 for exemplary sequences of NMRK.

Figures 3A, 3B:
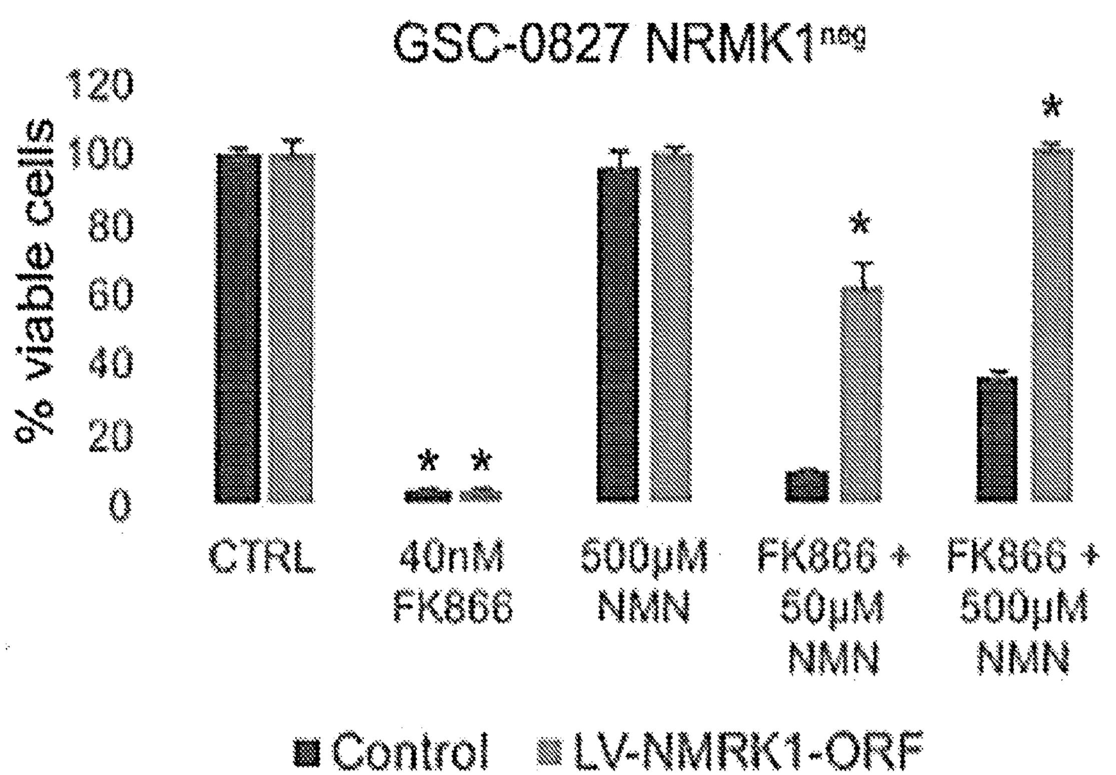
FIGS. 3A-3C. (3A) patient-derived GSC-0827 cells show little or no expression of NRMK1 (RNA-seq, CPM values) and their FK866-sensitivity cannot be overcome by exogenous NAD salvage pathway substrates such as NMM. (3B) Ectopic expression of NRMK1 from a lentivirus in GSC-0827 cells allows utilization of extracellular NMN. (3C) knockout of NRMK1 in GSC-0131 cells, which express NRMK1 and can be complemented with NMN after FK866 treatment, causes them to become sensitive to FK866+NMN.
Figure 3C:
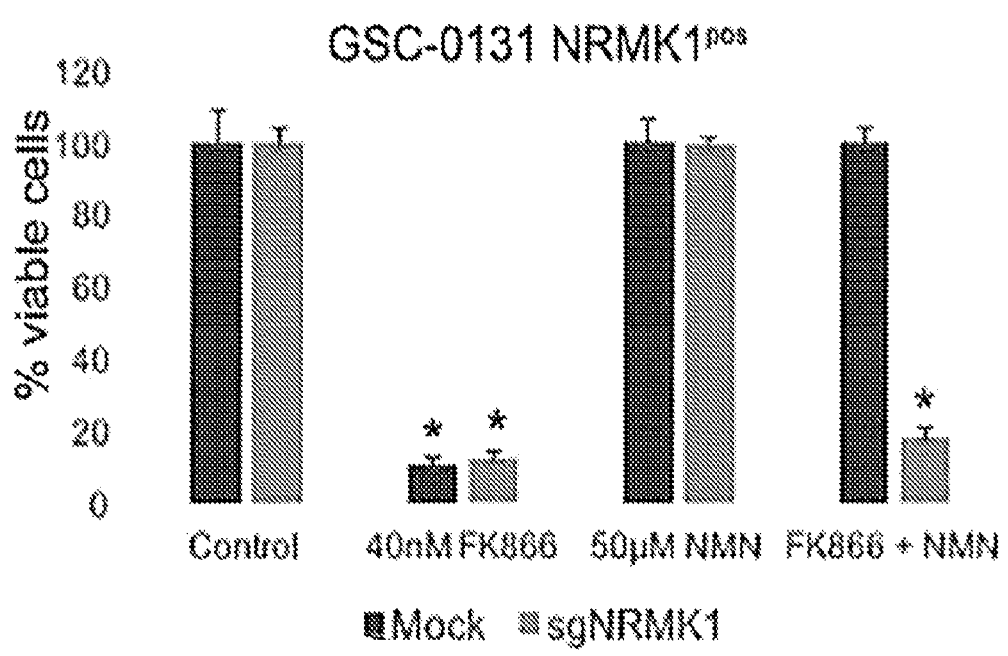
Figure 4:
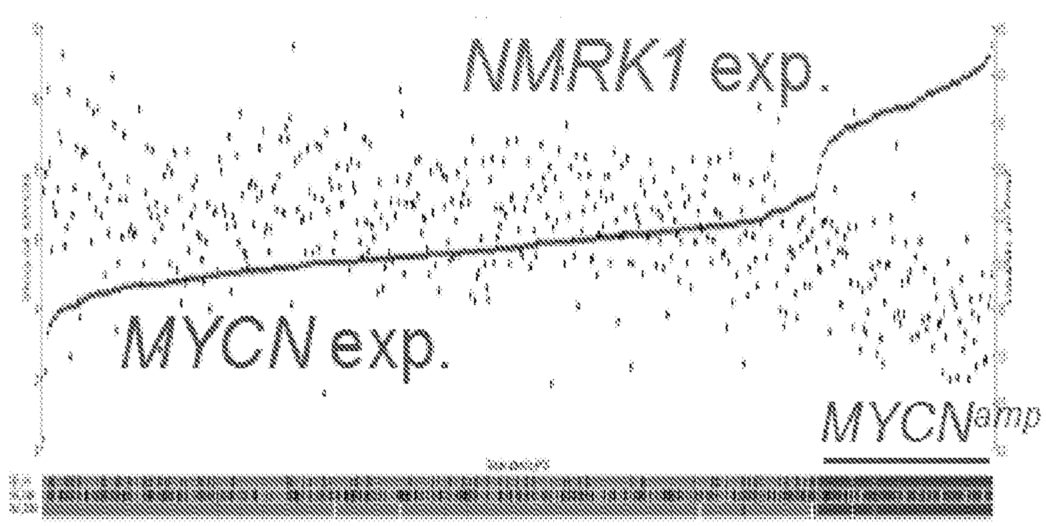
FIG. 4. Left panel: XY plot of MYCN expression (red line) versus NMRK1 expression (blue dots) across 498 neuroblastoma tumors (R2 database). Right panel: R2 and p values for MYCN and NMRK1 for multiple CNS/non-CNS cancer types (n>100 for each cancer).
Figures 5, 6:
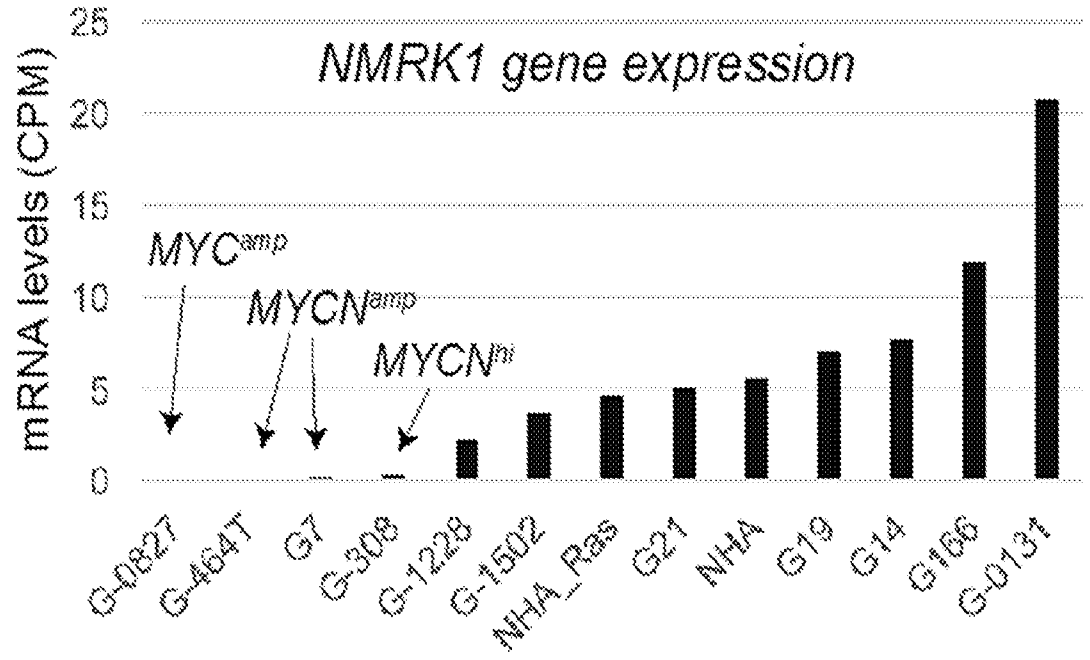
FIG. 5. Expression of NMRK1 in human GBM stem-like cells and normal human astrocytes (NHA).
FIG. 6. Select gene expression changes in NSC-CB660 cells after retroviral transduction with MMLV-hMYC. NMRK1 and OSTF1 share the same promoter, suggesting MYC directly or indirectly causes its repression.

An $NMRK^{low}$ status is observed in numerous brain tumor types, including neuroblastoma, low grade glioma, glioblastoma, and ependymoma (FIGS. 3A-3C). For example, examination of the cell line encyclopedia database (Broad/Sanger) and other resources, identified multiple examples of tumor-derived cells with low or absent expression of NMRK1, including multiple neuroblastoma derived lines (e.g., nb-1 [JCRB #IFO50295], SH-SY5Y [ATCC #2266], SK-N-FI [ATCC #CRL-2142], SiMa [DSMZ #ACC164]) and other cancer types including acute lymphocytic leukemia, chronic myeloid leukemia, esophageal cancer, non-small cell and small cell lung carcinoma, osteosarcoma, ovarian germ cell tumor, and pancreatic ductal carcinoma. From gene expression databases, it was also found that 5-20% of brain tumor types show $NMRK1^{low}$ expression and also show a significant negative correlation with MYC/MYCN expression (see, e.g., FIG. 4).

The MYC gene family encodes three different transcription factors, c-Myc (encoded by MYC), N-Myc (encoded by MYCN) and L-Myc (encoded by MYCL), respectively, which regulate a wide array of genes and cellular processes. The Myc protein acts through binding of Enhancer Box sequences (E-boxes) and also by recruiting histone acetyltransferases (HATs), thus regulating the chromatin structure. Myc is believed to regulate expression of 15% of all human genes. Myc also drives cell proliferation (e.g. by upregulating cyclins, E2F transcription factors and downregulating p21), and it plays an important role in regulating cell growth (upregulating ribosomal RNA and proteins), apoptosis (downregulating Bcl-2), differentiation and stem cell self-renewal. The MYC gene family is activated in 25-35% of all human cancers.

In particular embodiments, high and low expression of NMRK and/or Myc in a subject sample can be determined using any appropriate laboratory technique, such as polymerase chain reaction (PCR), deep sequencing, immunohistochemistry (IHC), enzyme linked immunosorbent assays (ELISA), flow cytometry or fluorescence-activated cell-sorting (FACs).

Reagents are commercially available to measure NMRK and Myc expression levels. For example, Santa Cruz Biotechnology offers a Mouse Anti-NMRK1 monoclonal antibody (Product: sc-398852 AC). Origene offers the ITGB1BP3 Antibody (OTI3H9) under Catalog #CF813058 with reactivity against human against NMRK2.

Primers and probes to detect NMRK expression can be purchased as Assay on Demand (FAM) products from Applied Biosystems. Exemplary primers to detect NMRK1 expression include NMRK1 Human qPCR Primer Pair (NM_017881; Origene CAT #: HP212669):

```
Forward Sequence:
                                  (SEQ ID NO: 13)
CCAAATTGCAGTGTCATATCTCAG
and

Reverse Sequence:
                                  (SEQ ID NO: 14)
CCAGCAGGAAATGGCTGACATC.
```

Exemplary primers to detect NMRK2 expression include NMRK2 Human qPCR Primer Pair (NM_170678; Origene CAT #: CAT #: HP228964

```
Forward Sequence:
                                    (SEQ ID NO: 15)
CCATGTACCAGAAGTATAGGCAG
and

Reverse Sequence:
                                    (SEQ ID NO: 16)
GCGAGTTCTGAATGTCTTCCAGG.
```

Additionally, Western blot and PCR methods and reagents to detect NMRK1/2 are described in Fletcher et al., Molecular Metabolism, 6(8) (2017) 819-832. For example, antibodies specific for NMRK1/2 were generated and affinity purified by BioGenes (GmbH) Berlin, Germany.

Regarding Myc, antibodies are commercially available from Invitrogen (cMyc monoclonal antibody 9E10; Catalog #13-2500; nMyc monoclonal antibody NCM-II 100; Catalog #MA1-170).

Primers and probes to detect Myc expression are also available. For example, there is the MYC human qPCR primer pair from Origene ((NM_002467; CAT #: HP206146):

```
Forward Sequence:
                                    (SEQ ID NO: 17)
CCTGGTGCTCCATGAGGAGAC
and

Reverse Sequence:
                                    (SEQ ID NO: 18)
CAGACTCTGACCTTTTGCCAGG
```

as well as the MYCN Human qPCR Primer Pair (NM_005378; CAT #: HP208523), also from Origene:

```
Forward Sequence:
                                    (SEQ ID NO: 19)
ACCACAAGGCCCTCAGTACCTC
and

Reverse Sequence:
                                    (SEQ ID NO: 20)
TGACAGCCTTGGTGTTGGAGGA.
```

Further, as is understood by one of ordinary skill in the art of flow cytometry, "high", "low", "+" and "−" refer to the intensity of a signal relative to negative or other populations. In particular embodiments, positive expression (+) means that the marker is detectable on a cell using flow cytometry. In particular embodiments, negative expression (−) means that the marker is not detectable using flow cytometry. In particular embodiments, "high" means that the positive expression of a marker of interest is brighter as measured by fluorescence (using for example FACS) than other cells also positive for expression. In these embodiments, those of ordinary skill in the art recognize that brightness is based on a threshold of detection. Generally, one of skill in the art will analyze a negative control tube first, and set a gate (bitmap) around the population of interest by forward scatter (FSC) and side scatter (SSC) and adjust the photomultiplier tube voltages and gains for fluorescence in the desired emission wavelengths, such that 97% of the cells appear unstained for the fluorescence marker with the negative control. Once these parameters are established, stained cells are analyzed and fluorescence recorded as relative to the unstained fluorescent cell population. In particular embodiments, and representative of a univariate, or single antigen, FACS plot, hi implies to the farthest right (x axis of histogram) while lo implies lesser shifts to the right (but shifted relative to the negative population). The y-axis of the histogram indicates the count, number of events, or cell count.

In particular embodiments, and representative of a bivariate, or two antigen, FACS plot, a dot or density plot describes one marker on each of the x- and y-axes. The relative proportion of cells double positive, double negative, or positive for either marker can be determined or quantified by placing gates or quadrants around the distinct populations. In bivariate FACs plots, shifts up or to the right indicate high expression of respective marker.

Particular embodiments utilize median fluorescent intensity (MFI) representing the strength of detection signal on cells, which in turn is related to the number of NMRK and/or Myc binding constructs bound to the cells.

In particular embodiments, "high" refers to greater than 20-fold of +, greater than 30-fold of +, greater than 40-fold of +, greater than 50-fold of +, greater than 60-fold of +, greater than 70-fold of +, greater than 80-fold of +, greater than 90-fold of +, greater than 100-fold of +, or more of an increase in detectable fluorescence relative to + cells. Conversely, "lo" can refer to a reciprocal population of those defined as "high". In particular embodiments, high is ≥5× a defined lower limit. In particular embodiments, low is ≤5× a defined high limit.

In particular embodiments, an $NMRK^{low}$ status indicates that the expression level of NMRK in the sample is similar to or characteristic of tumors or cancer cells in which NMRK is not constitutively activated. In particular embodiments, an $NMRK^{low}$ status indicates that the expression level of NMRK in the sample is similar to or characteristic of tumors or cancer cells in which NMRK is not overexpressed. In particular embodiments, an $NMRK^{low}$ status indicates that the expression level of NMRK in the sample is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more lower than that in tumors or cancer cells in which NMRK is not constitutively activated or NMRK is not overexpressed.

In particular embodiments, a $Myc^{high}$ status indicates that the expression level of Myc in a sample is similar to or characteristic of tumors or cancer cells overexpressing Myc. In particular embodiments, a $Myc^{high}$ status indicates that the expression level of Myc in the sample is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher than that in tumors or cancer cells in which Myc is not overexpressed. In particular embodiments, $MyC^{high}$ indicates MYC/MYCL/$MYCN^{high}$.

In particular embodiments, tumor samples can be scored for cell membrane staining intensity (on a scale of 1+ to 3+). The fraction of tumor cells in the sample staining at each intensity can also be obtained. Membrane staining can graded as follows: 0=no staining; 1+=weak staining visible only at high magnification; 2+=between 1+ and 3+; 3+=dark linear membrane staining visible with low magnification. In particular embodiments, the intensity of staining can be integrated with the frequency of staining in the tumor sample. An immunochemistry (IHC) score on a scale of 1-300 for each tumor sample can be calculated using the formula: 1×(percentage of cells staining 1+)+2×(percentage of cells staining 2+)+3×(percentage of cells staining 3+), giving a maximum score of 300 (for 100% of cells staining 3+). In particular embodiments, tumor having IHC scores of 200 or higher can be considered to be high-expressing tumors. In particular embodiments, tumor having IHC scores of 100 or lower can be considered to be low-expressing tumors.

In particular embodiments, expression of a protein or nucleic acid can be scored as positive/high or negative/low relative to a control sample that is used to calibrate the expression level of the protein or nucleic acid. In particular embodiments, the control sample can be known in the field of cancer biology as having a generally accepted expression characteristic for the given marker (e.g., positive/high or negative/low).

NAMPT & NAMPT Inhibitors. As indicated, NAMPT plays a key role in the biosynthesis of NAD in mammalian cells, and is the rate-limiting enzyme that catalyzes the first reaction of the synthesis of NAD from nicotinamide.

Numerous NAMPT inhibitors have been developed and can be used within the teachings of the current disclosure. As indicated, in particular embodiments, NAMPT inhibitors include FK866, CHS-828, GNE-617, GNE-618, STF118804, KPT-9274, and/or LSN3154567. However, there are numerous additional NAMPT inhibitors that can be used within the combination therapies disclosed herein. For example, additional examples of NAMPT inhibitors are described in U.S. Pat. No. 9,555,039 and include:

N-(4-{1-[(3,5-dichlorophenyl)carbonyl]piperidin-4-yl}butyl)thieno[2,3-c]pyridine-2-carboxamide,
N-(4-{1-[(3-fluoro-4-methoxybenzene)sulfonyl]piperidin-4-yl}butyl)-1H-pyrrolo[3,2-c]pyridine-2-carboxamide,
N-[4-(1-{[2-(trifluoromethoxy)benzene]sulfonyl}piperidin-4-yl)butyl]-1H-pyrrolo[3,2-c]pyridine-2-carboxamide,
N-[4-(1-{[4-(trifluoromethyl)phenyl]carbonyl}piperidin-4-yl)butyl]imidazo-[1,2-a]pyridine-6-carboxamide,
N-[4-(1-{[6-(morpholin-4-yl)pyridin-3-yl]carbonyl}piperidin-4-yl)butyl]-1-H-pyrrolo[3,2-c]pyridine-2-carboxamide,
N-(4-{1-[(dimethyl-1,3-thiazol-5-yl)carbonyl]piperidin-4-yl}butyl)-1H-pyrrolo[3,2-c]pyridine-2-carboxamide,
N-[4-(1-cyclohexanecarbonylpiperidin-4-yl)butyl]-1H-pyrrolo[3,2-c]pyridine-2-carboxamide,
N-[4-(1-{[4-(propan-2-yloxy)phenyl]carbonyl}piperidin-4-yl)butyl]imidazo[-1,2-a]pyridine-6-carboxamide,
N-(4-{1-[(2-fluorophenyl)carbonyl]piperidin-4-yl}butyl)-1H-pyrrolo[3,2-c]-pyridine-2-carboxamide,
N-(4-{1-[(1H-indol-2-yl)carbonyl]piperidin-4-yl}butyl)-1H-pyrrolo[3,2-c]pyridine-2-carboxamide,
N-(4-{1-[(4-chloro-2-methoxyphenyl)carbonyl]piperidin-4-yl}butyl)imidazo[-1,2-a]pyridine-6-carboxamide,
N-(4-{1-[(2,4-difluorophenyl)carbonyl]piperidin-4-yl}butyl)imidazo[1,2-a]-pyridine-6-carboxamide,
N-{4-[1-(propane-2-sulfonyl)piperidin-4-yl]butyl}-1H-pyrrolo[3,2-c]pyridine-2-carboxamide,
N-(4-{1-[2-(2-methyl-1,3-thiazol-4-yl)acetyl]piperidin-4-yl}butyl)imidazo-[1,2-a]pyridine-6-carboxamide,
N-(4-{1-[(1-methyl-1H-imidazol-4-yl)carbonyl]piperidin-4-yl}butyl)-1H-pyrrolo[3,2-c]pyridine-2-carboxamide,
N-(4-{1-[(5-fluoropyridin-2-yl)carbonyl]piperidin-4-yl}butyl)thieno[2,3-c-]pyridine-2-carboxamide,
N-(4-{1-[(dimethyl-1,3-thiazol-5-yl)carbonyl]piperidin-4-yl}butyl)imidazo-[1,2-a]pyridine-6-carboxamide,
N-(4-{1-[(2-fluoro-3-methylphenyl)carbonyl]piperidin-4-yl}butyl)thieno[2,-3-c]pyridine-2-carboxamide,
N-(4-{1-[(3-ethoxyphenyl)carbonyl]piperidin-4-yl}butyl)thieno[2,3-c]pyridine-2-carboxamide,
N-(4-{1-[(4-chlorophenyl)carbonyl]piperidin-4-yl}butyl)-1H-pyrrolo[3,2-c]-pyridine-2-carboxamide,
N-(4-{1-[(4-fluorophenyl)carbonyl]piperidin-4-yl}butyl)imidazo[1,2-a]pyridine-6-carboxamide,
N-(4-{1-[(pyridin-3-yl)carbonyl]piperidin-4-yl}butyl)-1H-pyrrolo[3,2-c]pyridine-2-carboxamide,
N-[4-(1-{[4-(propan-2-yloxy)benzene]sulfonyl}piperidin-4-yl)butyl]-1H-pyrrolo[3,2-c]pyridine-2-carboxamide,
N-(4-{1-[(2,5-dichlorophenyl)carbonyl]piperidin-4-yl}butyl)imidazo[1,2-a]-pyridine-6-carboxamide, and
N-(4-{1-[(2,6-dimethoxyphenyl)carbonyl]piperidin-4-yl}butyl)thieno[2,3-c]-pyridine-2-carboxamide, among many others.

Additional examples of NAMPT inhibitors include the pyridyloxyacetyl tetrahydroisoquinoline compounds as described in US20160229835. Exemplary compounds described in US20160229835 include tert-Butyl 6-(methanesulfonamido)-3,4-dihydro-1H-isoquinoline-2-carboxylate,
tert-Butyl 6-(2-methoxyethylsulfonylamino)-3,4-dihydro-1H-isoquinoline-2-carboxylate,
tert-Butyl 6-[(2-hydroxy-2-methyl-propyl)sulfonylamino]-3,4-dihydro-1H-isoquinoline-2-carboxylate,
tert-Butyl 6-(2-isopropoxyethylsulfonylamino)-3,4-dihydro-1H-isoquinoline-2-carboxylate,
tert-Butyl 6-[(3-hydroxy-3-methyl-pentanoyl)amino]-3,4-dihydro-1H-isoquinoline-2-carboxylate,
tert-Butyl6-[(4,4,4-trifluoro-3-hydroxy-3-methyl-butanoyl)amino]-3,4-dihydro-1H-isoquinoline-2-carboxylate,
2-Hydroxy-2-methyl-N-(1,2,3,4-tetrahydroisoquinolin-6-yl)propane-1-sulfonamide hydrochloride,
2-Methoxy-N-(1,2,3,4-tetrahydroisoquinolin-6-yl)ethanesulfonamide hydrochloride,
1,2,3,4-Tetrahydroisoquinolin-6-amine,
1-(6-Amino-3,4-dihydro-1H-isoquinolin-2-yl)-2-(3-pyridyloxy)ethenone,
tert-Butyl 4-[[2-[2-(3-pyridyloxy)acetyl]-3,4-dihydro-1H-isoquinolin-6-yl]-sulfamoyl]piperidine-1-carboxylate,
N-[2-[2-(3-Pyridyloxy)acetyl]-3,4-dihydro-1H-isoquinolin-6-yl]piperidine-4-sulfonamide,
6-Hydroxymethyl-3,4-dihydro-1H-isoquinoline-2-carboxylic acid tert-butyl ester,
tert-Butyl 6-formyl-3,4-dihydro-1H-isoquinoline-2-carboxylate,
tert-Butyl 6-[methoxy(methyl)carbamoyl]-3,4-dihydro-1H-isoquinoline-2-carboxylate,
tert-Butyl 6-acetyl-3,4-dihydro-1H-isoquinoline-2-carboxylate,
Piperazin-1-yl(tetrahydropyran-4-yl)methanone,
2-Morpholino-1-piperazin-1-yl-ethanone,
tert-Butyl6-[[4-(tetrahydropyran-4-carbonyl)piperazin-1-yl]methyl]-3,4-di-hydro-1H-isoquinoline-2-carboxylate,
tert-Butyl6-[[4-(3-hydroxy-3-methyl-butanoyl)piperazin-1-yl]methyl]-3,4-dihydro-1H-isoquinoline-2-carboxylate,
tert-Butyl 6-[1-[4-(tetrahydropyran-4-carbonyl)piperazin-1-yl]ethyl]-3,4-dihydro-1H-isoquinoline-2-carboxylate,
[4-(1,2,3,4-Tetrahydroisoquinolin-6-ylmethyl)piperazin-1-yl]-tetrahydropyran-4-yl-methanone,
[4-[1-(1,2,3,4-Tetrahydroisoquinolin-6-yl)ethyl]piperazin-1-yl]-tetrahydropyran-4-yl-methanone,
2-Morpholino-1-[4-(1,2,3,4-tetrahydroisoquinolin-6-ylmethyl)piperazin-1-yl-]ethenone,
2-Hydroxy-2-methyl-N-[2-[2-(3-pyridyloxy)acetyl]-3,4-dihydro-1H-isoquinolin-6-yl]propane-1-sulfonamide,
and
2-Methoxy-N-[2-[2-(3-pyridyloxy)acetyl]-3,4-dihydro-1H-isoquinolin-6-yl]ethanesulfonamide crystalline anhydrous free base, among many others.

Additional examples of NAM PT inhibitors include the 1,3-dihydro-2H-isoindole compounds as described in U.S.

Pat. No. 9,302,989. Exemplary compounds described in U.S. Pat. No. 9,302,989 include N-(4-{[(3S)-tetrahydrofuran-3-ylmethyl] carbamoyl}phenyl)-1,3-dihydro-2H-isoindole-2-carboxamide, 5-fluoro-N-(4-{[(3S)-tetrahydrofuran-3-ylmethyl] carbamoyl}phenyl)-1,3-dihydro-2H-isoindole-2-carboxamide, N-(4-{[(3S)-tetrahydrofuran-3-ylmethyl] carbamoyl}phenyl)-1,3-dihydro-2H-isoindole-2-carboxamide, N-[4-(1-benzoylpiperidin-4-yl)butyl]-1,3-dihydro-2H-isoindole-2-carboxamide, N-{4-[1-(pyridin-3-ylcarbonyl)piperidin-4-yl]butyl}-1,3-dihydro-2H-isoindole-2-carboxamide, N-[4-(1-benzoylpiperidin-4-yl)butyl]-5-cyano-1,3-dihydro-2H-isoindole-2-carboxamide, N-{4-[1-(pyridin-2-ylcarbonyl)piperidin-4-yl]butyl}-1,3-dihydro-2H-isoindole-2-carboxamide, N-{4-[(3-phenylpropyl)carbamoyl]phenyl}-1,3-dihydro-2H-isoindole-2-carboxamide, N-(4-{[4-(aminomethyl)benzyl]carbamoyl}phenyl)-5-fluoro-1,3-dihydro-2H-isoindole-2-carboxamide, 5-cyano-N-{4-[(3-phenylpropyl)carbamoyl]phenyl}-1,3-dihydro-2H-isoindole-2-carboxamide, N-{4-[(cyclopentylmethyl)carbamoyl]phenyl)-5-fluoro-1,3-dihydro-2H-isoindole-2-carboxamide, 5-cyano-N-[4-(propylcarbamoyl)phenyl]-1,3-dihydro-2H-isoindole-2-carboxamide, N-(4-{[4-(furo[3,2-c]pyridin-4-yl)piperazin-1-yl] carbonyl}phenyl)-1,3-dihydro-2H-isoindole-2-carboxamide, 5-cyano-N-(4-[4-(pyridin-2-yl)piperazin-1-yl] carbonyl}phenyl)-1,3-dihydro-2H-isoindole-2-carboxamide, 5-fluoro-N-{4-[(pyridin-2-ylmethyl)carbamoyl]phenyl}-1, 3-dihydro-2H-isoindole-2-carboxamide, N-[4-(benzylcarbamoyl)phenyl]-5-fluoro-1,3-dihydro-2H-isoindole-2-carboxamide, N-{4-[(3,4-dimethoxybenzyl)carbamoyl]phenyl}-1,3-dihydro-2H-isoindole-2-carboxamide, 5-methyl-N-(4-{[4-(pyridin-2-yl)piperazin-1-yl] carbonyl}phenyl)-1,3-dihydro-2H-isoindole-2-carboxamide, N-(4-{[4-(thieno[3,2-c]pyridin-4-yl)piperazin-1-yl] carbonyl}phenyl)-1,3-dihydro-2H-isoindole-2-carboxamide, N-{4-[(2,3-dimethoxybenzyl)carbamoyl]phenyl}-1,3-dihydro-2H-isoindole-2-carboxamide, 5-fluoro-N-{4-[(3-phenylpropyl)carbamoyl]phenyl}-1,3-dihydro-2H-isoindole-2-carboxamide, 5-fluoro-N-(4-{[4-(pyridazin-311)piperazin-1-yl]carbonyl) }phenyl)-1,3-dihydro-2H-isoindole-2-carboxamide, N-{4-[(2,3-dihydro-1,4-benzodioxin-5-ylmethyl)carbamoyl]phenyl}-1,3-dihydro-2-isoindole-2-carboxamide, 5-fluoro-N-(4-{[1-(3-methylbutyl)-1H-pyrazol-4-yl] carbamoyl}phenyl)-1,3-dihydro-2H-isoindole-2-carboxamide, N-{4-[(2-fluorobenzyl)carbamoyl]phenyl}-1,3-dihydro-2H-isoindole-2-carboxamide, and N-{4-[(3-butoxypropyl)carbamoyl]phenyl}-1,3-dihydro-2H-isoindole-2-carboxamide, among many others.

Additional examples of NAMPT inhibitors include the 4,5-dihydroisoxazole derivative compounds as described in WO2014111871. Exemplary compounds described in WO20141118719 include I-((5-(([I,I'-biphenyl]-2-yloxy)methyl)-4,5-dihydroisoxazol-3-yl)methyl)-3-(pyridin-3-yl) urea (±), I-((5-(([I,I'-biphenyl]-2-yloxy)methyl)-4,5-dihydroisoxazol-3-yl)methyl)-3-(pyridin-4-yl) urea (±), I-((5-(([I,I'-biphenyl]-2-yloxy)methyl)-4,5-dihydroisoxazol-3-yl)methyl)-3-a(pyridin-4-yl) urea, I-((5-(([I,I'-biphenyl]-2-yloxy)methyl)-4,5-dihydroisoxazol-3-yl)methyl)-3-b(pyridin-4-yl) urea, I-((5-(([I,I'-biphenyl]-2-yloxy)methyl)-4,5-dihydroisoxazol-3-yl)methyl)-2-cyano-3-(pyridin-4-yl) guanidine (±), N-((5-(([I,I'-biphenyl]-2-yloxy)methyl)-4,5-dihydroisoxazol-3-yl)methyl)-6,7-dihydrothieno [3,2-c]pyridine-5 (4H)-carboxamide (±), N-((5-(([I,I'-biphenyl]-2-yloxy)methyl)-4,5-dihydroisoxazol-3-yl)methyl)-6,7-a dihydrothieno [3,2-c]pyridine-5 (4H)-carboxamide, N-((5-(([I,-biphenyl]-2-yloxy)methyl)-4,5-dihydroisoxazol-3-yl)methyl)-6,7-b dihydrothieno [3,2-c]pyridine-5 (4H)-carboxamide, N-((5-(([I,I'-biphenyl]-2-yloxy)methyl)-4,5-dihydroisoxazol-3-yl)methyl)-3,4-dihydroisoquinoline-2(IH)-carboxamide (±), I-((5-(([I,I'-biphenyl]-2-yloxy)methyl)-4,5-dihydroisoxazol-3-yl)methyl)-3-(pyridin-3-ylmethyl) urea (±), I-((3-((2-bromophenoxy)methyl)-4,5-dihydroisoxazol-5-yl) methyl)-3-(pyridin-3-yl) urea (±), I-((3-(([I,I'-biphenyl]-2-yloxy)methyl)-5-methyl-4,5-dihydroisoxazol-5-yl)methyl)-3-(pyridin-3-yl) urea (±), I-((3-(([I,I'-biphenyl]-2-yloxy)methyl)-5-methyl-4,5-dihydroisoxazol-5-yl)methyl)-3-(pyridin-4-yl) urea (±), I-((3-(([I,I'-biphenyl]-2-yloxy)methyl)-5-methyl-4,5-dihydroisoxazol-5-yl)methyl)-3-(pyridin-3-ylmethyl) urea (±), I-((3-(([I,I'-biphenyl]-2-yloxy)methyl)-5-methyl-4,5-dihydroisoxazol-5-ayl)methyl)-3-(pyridin-3-ylmethyl) urea, I-((3-(([I,I'-biphenyl]-2-yloxy)methyl)-5-methyl-4,5-dihydroisoxazol-5-byl)methyl)-3-(pyridin-3-ylmethyl) urea, I-((5-(([I,I'-biphenyl]-2-yloxy)methyl)-4,5-dihydroisoxazol-3-yl)methyl)-3-(2-fluoropyridin-4-yl) urea (±), I-((5-(([I,I'-biphenyl]-2-yloxy)methyl)-4,5-dihydroisoxazol-3-yl)methyl)-3-(2-chloropyridin-4-yl) urea (±), I-((5-(([I,I'-biphenyl]-2-yloxy)methyl)-4,5-dihydroisoxazol-3-yl)methyl)-3-(2-methylpyridin-4-yl) urea (±), I-((5-(([I,I'-biphenyl]-2-yloxy)methyl)-4,5-dihydroisoxazol-3-yl)methyl)-3-a(2-methylpyridin-4-yl) urea (±), I-((5-(([I,I'-biphenyl]-2-yloxy)methyl)-4,5-dihydroisoxazol-3-yl)methyl)-3-b-(2-methylpyridin-4-yl) urea (±), I-((5-(([I,I'-biphenyl]-2-yloxy)methyl)-4,5-dihydroisoxazol-3-yl)methyl)-3-(3-cyanophenyl) urea (±), I-((5-(([I,I'-biphenyl]-2-yloxy)methyl)-4,5-dihydroisoxazol-3-yl)methyl)-3-(furan-2-ylmethyl) urea (±), I-((5-(([I,I'-biphenyl]-2-yloxy)methyl)-4,5-dihydroisoxazol-3-yl)methyl)-3-(4-cyanophenyl) urea (±), I-((5-(([I,I'-biphenyl]-2-yloxy)methyl)-4,5-dihydroisoxazol-3-yl)methyl)-3-a(4-cyanophenyl) urea, and I-((5-((2-(I-methyl-IH-pyrazol-4-yl)phenoxy)methyl)-4,5-dihydroisoxazol-3-yl)methyl)-3-(pyridin-4-yl) urea (±), among many others.

Additional examples of NAMPT inhibitors include the 1,4-disubstituted triazoles with substitution compounds as described in US20160075682. Exemplary compounds described in US20160075682 include 2-bromo-N-(6-(4-(pyridin-3-yl)-1H-1,2,3-triazol-1-yl) hexyl)benzenesulfonamide, N-(6-(4-(pyridin-3-yl)-1H-1,2,3-triazol-1-yl)hexyl)-[1,1'-biphenyl]-2-sulfonamide, 2'-((6-(4-(pyridin-3-yl)-1H-1,2,3-triazol-1-yl)hexyl)oxy)-[1,1'-biphenyl]-4-carboxylic acid,
2'-((6-(4-(pyridin-3-yl)-1H-1,2,3-triazol-1-yl)hexyl)oxy)-[1,1'-biphenyl]-3-carboxylic acid,
2-bromo-N-(7-(4-(pyridin-3-yl)-1H-1,2,3-triazol-1-yl)heptyl)benzenesulfonamide,
2-iodo-N-(7-(4-(pyridin-3-yl)-1H-1,2,3-triazol-1-yl)heptyl)benzamide,
N-(7-(4-(pyridin-3-yl)-1H-1,2,3-triazol-1-yl)heptyl)-[1,1'-biphenyl]-2-sulfonamide,
2'-((7-(4-(pyridin-3-yl)-1H-1,2,3-triazol-1-yl)heptyl)carbamoyl)-[1,1'-biphenyl]-4-carboxylic acid,
3-(2-((6-(4-(pyridin-3-yl)-1H-1,2,3-triazol-1-yl)hexyl)oxy)phenyl)pyridine,
2-(pyridin-3-yl)-N-(7-(4-(pyridin-3-yl)-1H-1,2,3-triazol-1-yl)heptyl)benzamide,
3-(1-(8-([1,1'-biphenyl]-2-yloxy)octyl)-1H-1,2,3-triazol-4-yl)pyridine,
3-(1-(7-([1,1'-biphenyl]-2-yloxy)heptyl)-1H-1,2,3-triazol-4-yl)pyridine,
N-(7-(4-(pyridin-3-yl)-1H-1,2,3-triazol-1-yl)heptyl)-[1,1'-biphenyl]-2-carboxamide,
3-(1-(6-([1,1'-biphenyl]-2-yloxy)hexyl)-1H-1,2,3-triazol-4-yl)pyridine,
N-(6-(4-(pyridin-3-yl)-1H-1,2,3-triazol-1-yl)hexyl)[1,1'-biphenyl-]-2-carboxamide,
2'-((7-(4-(pyridin-3-yl)-1H-1,2,3-triazol-1-yl)heptyl)carbamoyl)-[1,1'-bi-phenyl]-2-carboxylic acid,
3-(1-(6-((2'-methyl-[1,1'-biphenyl]-2-yl)oxy)hexyl)-1H-1,2,3-triazol-4-yl-)pyridine,
2'-methyl-N-(7-(4-(pyridin-3-yl)-1H-1,2,3-triazol-1-yl)heptyl)-[-1,1'-biphenyl]-2-carboxamide,
N-([1,1'-biphenyl]-2-ylmethyl)-7-(4-(pyridin-3-yl)-1H-1,2,3-triazol-1-yl)-heptan-1-amine,
N-([1,1'-biphenyl]-2-ylmethyl)-6-(4-(pyridin-3-yl)-1H-1,2,3-triazol-1-yl)-hexan-1-amine,
1-([1,1'-biphenyl]-2-yl)-3-(6-(4-(pyridin-3-yl)-1H-1,2,3-triazol-1-yl)hexyl) urea,
1-([1,1'-biphenyl]-2-yl)-3-(7-(4-(pyridin-3-yl)-1H-1,2,3-triazol-1-yl)heptyl) urea,
6-(4-(pyridin-3-yl)-1H-1,2,3-triazol-1-yl)hexyl[1,1'-biphenyl]-2-ylcarbamate,
8-(4-(pyridin-3-yl)-1H-1,2,3-triazol-1-yl)octyl[1,1'-biphenyl]-2-ylcarbamate,
7-(4-(pyridin-3-yl)-1H-1,2,3-triazol-1-yl)heptyl[1,1'-biphenyl]-2-y-lcarbamate, and
N-(4-((4-(pyridin-3-yl)-1H-1,2,3-triazol-1-yl)methyl)phenethyl)-[1,1'-biphenyl]-2-sulfonamide, among many others.

Additional examples of NAMPT inhibitors include the quinoxaline, quinazoline and quinoline compounds as described in US20180009784 and U.S. Ser. No. 10/144,742. Exemplary compounds described in US20180009784 and U.S. Ser. No. 10/144,742 include
2-(4-chlorophenyl)-N-[2-(1-methyl-1H-imidazol-5-yl)ethyl]-4-propylquinazoline-7-carboxamide,
4-ethoxy-2-(4-fluorophenyl)-N-[2-(1-methyl-1H-imidazol-5-yl)ethyl]quinoline-7-carboxamide,
2-(4-chlorophenyl)-N-[cis-3-(1H-imidazol-2-yl)cyclobutyl]-4-propylquinazoline-7-carboxamide,
2-(4-chlorophenyl)-N-[3-(1H-imidazol-2-yl)propyl]-4-propylquinazoline-7-carboxamide,
4-ethoxy-2-(4-fluorophenyl)-N-[3-(4H-1,2,4-triazol-3-yl)propyl]quinoline-7-carboxamide,
4-ethoxy-2-(4-fluorophenyl)-N-[2-(1-methyl-1H-imidazol-4-yl)ethyl]quinoline-7-carboxamide,
2-(4-chlorophenyl)-4-propyl-N-[3-(4H-1,2,4-triazol-3-yl)propyl]quinazoline-7-carboxamide,
2-(4-chlorophenyl)-N-(imidazo[1,2-a]pyridin-6-ylmethyl)-4-propylquinazoline-7-carboxamide,
2-(4-chlorophenyl)-N-(3H-imidazo[4,5-c]pyridin-2-ylmethyl)-4-propylquinazoline-7-carboxamide,
2-(4-chlorophenyl)-N-[3-(1H-imidazol-2-yl)propyl]-4-methoxyquinazoline-7-carboxamide,
2-(5-chloro-2-fluorophenyl)-4-ethoxy-N-[3-(1H-imidazol-2-yl)propyl]quinoline-7-carboxamide,
4-ethoxy-2-(5-fluoro-2-methoxypyridin-4-yl)-N-[3-(1H-imidazol-2-yl)propyl]quinoline-7-carboxamide,
2-(4-chlorophenyl)-4-ethoxy-N-[3-(1H-imidazol-2H)propyl]quinoline-7-carboxamide
4-ethoxy-2-(4-fluorophenyl)-N-(1H-imidazo[4,5-c]pyridin-2-ylmethyl)quinoline-7-carboxamide,
4-ethoxy-2-(4-fluorophenyl)-N-[3-(1H-imidazol-2 yl) propyl]quinoline-7-carboxamide,
2-(4-fluorophenyl)-N-[3-(1H-imidazol-2-yl)propyl]-4-propylquinazoline-7-carboxamide,
2-(4-fluorophenyl)-N-[3-(1H-imidazol-2-yl)propyl]-4-isopropoxyquinoline-7-carboxamide,
4-ethoxy-2-(4-fluorophenyl)-N-[3-(1H-imidazol-2-yl)-2-methylpropyl]quinazoline-7-carboxamide,
4-ethoxy-2-(4-fluorophenyl)-N-[3-(pyrimidin-5-yl)propyl]quinazoline-7-carboxamide,
2-(4-chlorophenyl)-4-(ethoxymethyl)-N-[3-(1H-imidazol-2-yl)propyl]quinazoline-7-carboxamide,
2-(4-chlorophenyl)-N-[3-(1H-imidazol-2-yl)propyl]-4-isobutylquinazoline-7-carboxamide,
2-(5-chloro-2-thienyl)-4-ethyl-N-[3-(1H-imidazol-2-yl)propyl]quinazoline-7-carboxamide,
2-(5-chloro-2-thienyl)-N-[3-(1H-imidazol-2-yl)propyl]-4-isobutylquinazoline-7-carboxamide, and
4-ethoxy-2-(5-fluoro-2-methoxypyridin-4-yl)-N-[3-(4-methyl-1H-1,2,3-triazol-5-yl)propyl]quinoline-7-carboxamide, among many others.

Additional examples of NAMPT inhibitors include the 4-{[(pyridin-3yl-methyl) aminocarbonyl] amino} benzenesulfone derivative compounds as described in WO2012031196. Exemplary compounds described in WO2012031196 include
1-(pyridin-3-ylmethyl)-3-(4-{[2-(trifluoromethoxy)benzene]sulfonyl}phenyl) urea,
3-{4-[(4-bromobenzene)sulfonyl]phenyl}-1-(pyridin-3-ylmethyl) urea,
3-(4-{[2-methyl-4-(1H-pyrazol-1-yl)benzene]sulfonyl}phenyl)-1-(pyridin-3-ylmethyl) urea,
N-[2-(pyridin-3-yl)ethyl]-4-{[3-(trifluoromethoxy)benzene]sulfonyl}benzamide,
3-{4-[(4-methoxy-2-methylbenzene)sulfonyl]phenyl}-1-(pyridin-3-ylmethyl) urea,
3-{4-[(2,4-dimethoxybenzene)sulfonyl]phenyl}-1-(pyridin-3-ylmethyl) urea,
1-[(6-aminopyridin-3-yl)methyl]-3-{4-[(4-fluorobenzene)sulfonyl]phenyl} urea,
3-{4-[(3,5-dimethylbenzene)sulfonyl]phenyl}-1-(pyridin-3-ylmethyl) urea,
1-[(6-aminopyridin-3-yl)methyl]-3-[4-(benzenesulfonyl)phenyl] urea,
3-{4-[(4-methylbenzene)sulfonyl]phenyl}-1-(pyridin-3-ylmethyl) urea,
3-[4-(benzenesulfonyl)phenyl]-1-{[6-(1H-pyrazol-1-yl)pyridin-3-yl]methyl} urea,
3-(4-{[2-fluoro-4-(1H-pyrazol-1-yl)benzene]sulfonyl}phenyl)-1-(pyridin-3-ylmethyl) urea, 4-(benzenesulfonyl)-N-{imidazo[1,2-a]pyridin-7-ylmethyl}benzamide, 3-{4-[(2-bromobenzene)sulfonyl]phenyl}-1-(pyridin-3-yl-methyl) urea, 4-(benzenesulfonyl)-N-(pyridin-3-ylmethyl)benzamide, 3-{4-[(2-ethoxybenzene)sulfonyl]phenyl}-1-(pyridin-3-yl-methyl) urea, 3-[4-(benzenesulfonyl)phenyl]-1-{[6-(1H-imidazol-1-yl) pyridin-3-yl]methyl} urea, 3-{4-[(3,4-dimethoxybenzene)sulfonyl]phenyl}-1-(pyridin-3-ylmethyl) urea, 3-{[({4-[(4-chlorobenzene)sulfinyl]phenyl}carbamoyl) amino]methyl}pyridin-1-ium-1-olate, 1-(pyridin-3-ylmethyl)-3-(4-{[4-(trifluoromethyl)benzene] sulfonyl}phenyl) urea, 3-{4-[(2,5-dimethylbenzene)sulfonyl]phenyl}-1-(pyridin-3-ylmethyl) urea, 1-(pyridin-3-ylmethyl)-3-(4-{[3-(trifluoromethoxy)benzene]sulfonyl}phenyl) urea, N,N-dimethyl-4-[(4-{[(pyridin-3-ylmethyl)carbamoyl] amino}benzene)sulfonyl] benzamide, 3-(4-{[2-methoxy-4-(1H-pyrazol-1-yl)benzene] sulfonyl}phenyl)-1-(pyridin-3-ylmethyl) urea, 3-[4-(benzenesulfonyl)phenyl]-1-(pyridin-3-ylmethyl) urea, and 3-{4-[(4-chloro-2-fluorobenzene)sulfonyl]phenyl}-1-(pyridin-3-ylmethyl)urea, among many others.

Additional examples of NAMPT inhibitors include AU-4869 (Aurigene Discovery Technologies; under pre-clinical development for the treatment of pancreatic cancer and multiple myeloma); OT-82 (OncoTartis Inc; under development for the treatment of acute myeloblastic leukemia (AML), mixed lineage leukemia (MLL), acute lymphocytic leukemia, multiple myeloma and eryhthroleukemia) and the cluster boron moieties compounds as described in U.S. Pat. No. 9,382,267.

In particular embodiments, the activity of a compound to inhibit NAM PT can be confirmed using the following assay: Reaction mixtures (25 μL) containing 50 mM HEPES at pH 7.5, 50 mM NaCl, 1 mM DTT, 0.005% TRITON®X-100, 1.5 μM phosphoribosyl-pyrophosphate, 0.5 μM nicotinamide (NAM), 1.5 nM NAMPT, 2.5 mM ATP, 1.25 mM $MgCl_2$, 4% (v/v) DMSO and test compounds after a ten-point series dilution from either 1 μM to 50 μM or 0.1 μM to 5 μM (final) are prepared. The reaction mixtures are incubated at room temperature for 2 hours. The reaction is terminated by the addition of ACN (25 μL) containing NMN-$d_4$ as an internal standard (final concentration: 5 μM). The formation of NMN is quantified by a Liquid Chromatography-Mass Spectrometry (LC-MS) method as follows: NMN is analyzed on a Thermo Hypercarb Javelin column (2.1×20 mm, 5 μm) with an injection volume of 5 μL and a flow rate of 1 mL/minute using 0.1% formic acid for the mobile phase A and ACN for the mobile phase B. The gradient is as follows: 0 minutes, 0% B; 0.3 minutes, 0% B; 1.5 minutes, 35% B; 1.51 minutes, 95% B; 2.0 minutes, 95% B, 2.01 minutes, 0% B, 3 minutes, stop. A positive control group (enzyme and DMSO, but no compound) is used to measure minimum inhibition (0%) of NMN formation. Percent inhibition of compound treated groups is calculated relative to the minimum inhibition group. The relative $IC_{50}$ for each compound is calculated from a dose response study and is the concentration necessary to achieve 50% inhibition at this time point using the above disclosed ranges of 1 μM to 50 μM (final). The data generated from the dose-response studies is fit to a four-parameter logistic equation using ACTIVITYBASE 4.0 Equation 205. The results of this assay demonstrate compounds that inhibit NAMPT.

External Factors. As indicated, as disclosed herein, external factors allowing non-cancerous cells to utilize salvage pathways to create NAD are administered in coordination with NAM PT inhibitors.

In particular embodiments, the external factor is NMN, an intermediate metabolite of the coenzyme, NAD. However, NMN is a highly polar substance so modifying NMN for administration can be beneficial. For example, adding a lipophilic functional group into NMN improves bioavailability. Methods to synthesize a phosphodiester-type NMN, which is an NMN derivative having a lipophilic functional group are described in Liu et al., Tetrahedron, 65(40), 8378-8383 (2009). In addition, Liu et al describe synthesizing diacetyl NMN, a synthesis intermediate in which two hydroxyl groups of NMN are acetylated.

In particular embodiments, the external factor is NR (CAS Number 1341-23-7), a precursor to NAD that represents a source of vitamin B3. The chemical structure of NR includes

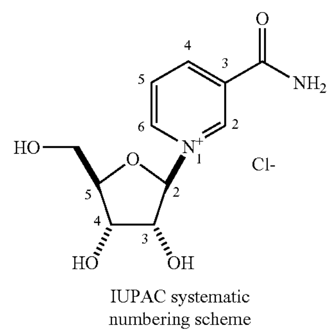

IUPAC systematic numbering scheme

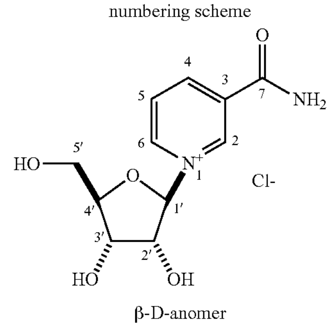

β-D-anomer

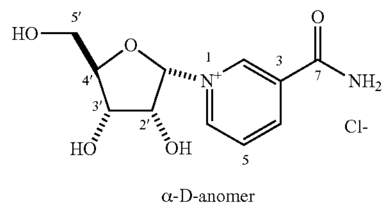

α-D-anomer

While NR itself is useful as an efficient precursor of NAD to elevate NAD levels, it can be difficult to isolate from natural sources. However, the first chemical synthesis of NR was described in Haynes et al., A. J. Chem. Soc. 1957, 3727-3732. The synthesis protocols described in Haynes et al., produce NR chloride as a mixture of α and β anomers about the glycosidic linkage in a 1:4 ratio. Methods for preparing NR from enriched natural sources, such as genetically engineered yeast strains are described in WO 2010/111111, and methods to produce various useful NR derivatives are described in U.S. Ser. No. 10/000,520 and US20060229265.

In particular embodiments, NR can be used in its reduced form (NRH) as a 1,4-dihydropyridine compound. Nicotinic acid riboside (NAR) and its reduced form (NARH) can also be used as external factors. For example, US20180362570 describes oxidized and reduced form of NR with improved stability and bioavailability compared to NR. Particularly described are compounds MP-05, MP-06, MP-07, MP-08, MP-09 and MP-10.

The bioavailability of NR under various modes of administration can be limited. Thus, particular embodiments can utilize modified NR analogues. One example of an NR analogue includes the NR chloride (3-carbamoyl-1-[(2R,3R,4S5R)-3,4-dihydroxy-5-(hydroxymethyl)oxolan-2-yl]-pyrin-1-ylium chloride; also referred to as 1-(β-D-Ribofuranosyl) nicotinamide chloride, which is a salt form of NR; see US20170210774). US20170204131 describes crystalline forms of NR chloride that are chemically stable. These crystalline forms of NR chloride include 3-carbamoyl-1-((2R,3R,4S,5R)-3,4-dihydroxy-5(hydroxymethyl)tetrahydrofuran-2-yl)pyridin-1-ium(β-D-NR) chloride crystal, 3-carbamoyl-1-((2R,3R,4S,5R)-3,4-dihydroxy-5(hydroxymethyl)tetrahydrofuran-2-yl)pyridin-1-ium(β-D-NR chloride methanolate crystal, and 3-carbamoyl-1-((2S,3R,4S,5R)-3,4-dihydroxy-5(hydroxymethyl)tetra hydrofuran-2-yl)pyridin-1-ium chloride. The first listed is more resistant to decomposition upon heating than other forms.

US20160272668 describes NR analogues that are better able to penetrate the skin than NR. Examples of these NR analogues include 1-(2',3',5'-triacetyl-beta-D-ribofuranosyl)-1,4-dihydronicotinic acid and 1-(2',3',5'-triacetyl-beta-D-ribofuranosyl)-1,4-nicotinamide.

U.S. Pat. No. 8,106,184 describes the following NR analogues with reduced potential toxicities: O-ethyl NR (OENR), tri-O-acetyl O'-ethyl NR (TAENR), N-dimethyl NR (DMNR), and N-allyl NR (ANR).

Additional NR analogues are described in US20170189433 and U.S. Ser. No. 10/000,519. Examples include:

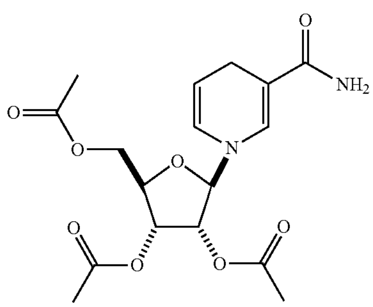

NRH triacetate

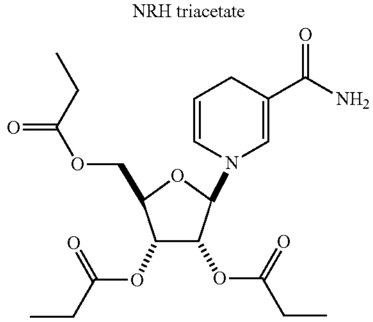

NRH triproprionate

-continued

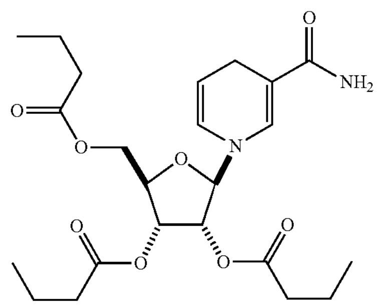

NRH tributyrate

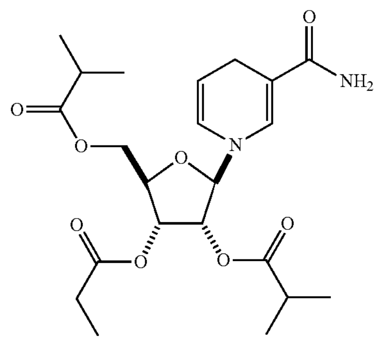

NRH triisobutyrate

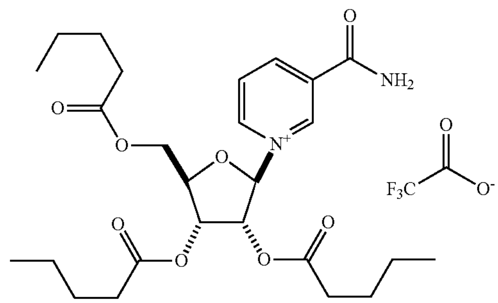

NR+ tripentanoate

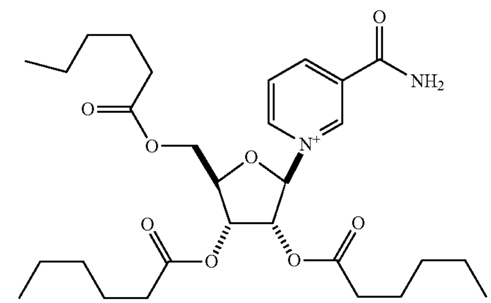

NR+ trihexanoate

-continued
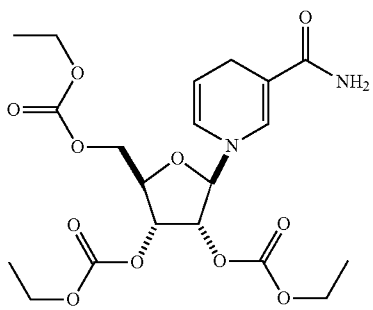
NRH triethylcarbonate
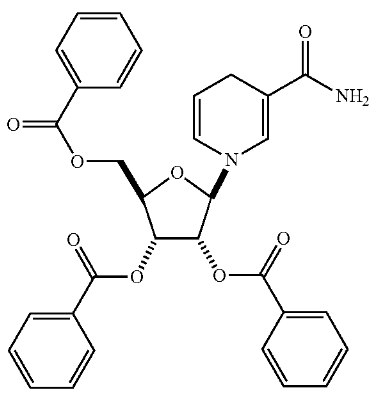
NRH tribenzoate
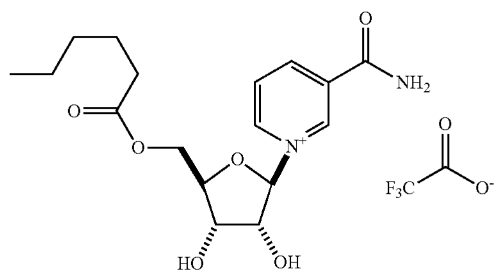
NR+ monohexanoate
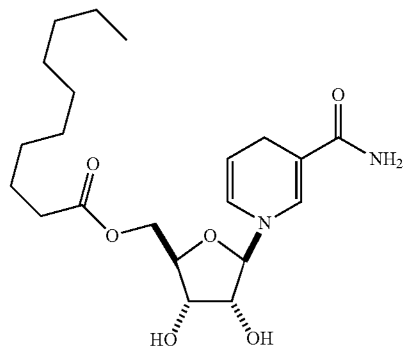
NRH monodecanoate
-continued
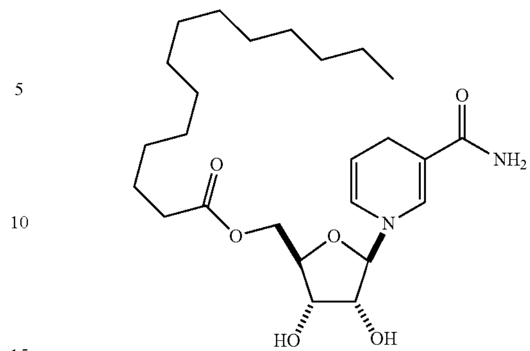
NRH monotetradecanoate
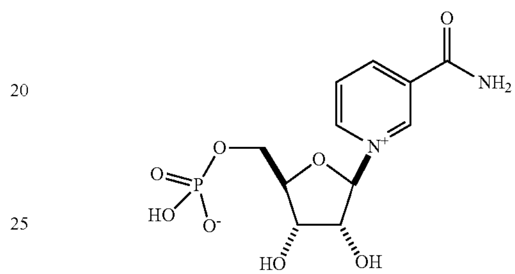
Nic mononucleotide (NMN)
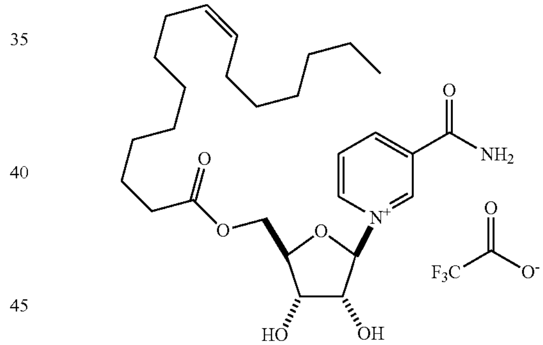
NR+ monooleate
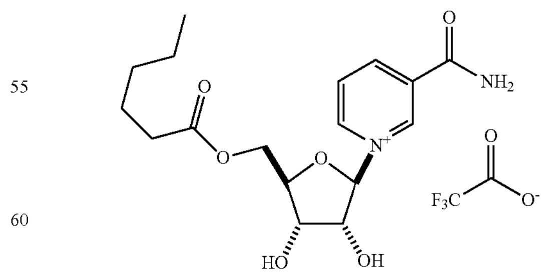
NR+ monohexanoate -continued

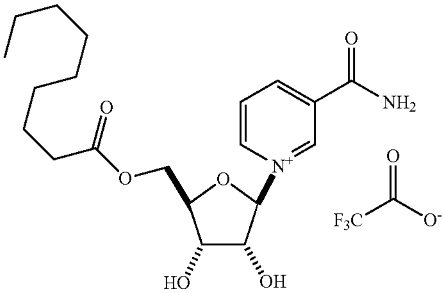

NR+ mononononanoate

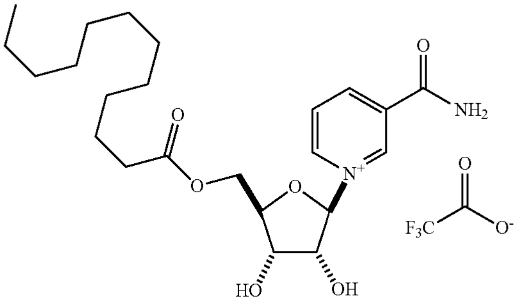

NR+ monododecanoate

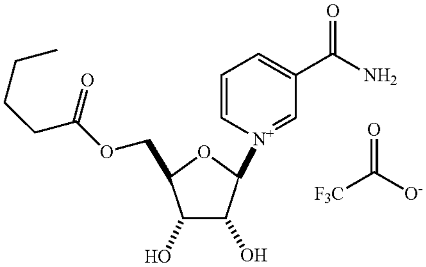

NR+ monopentanoate

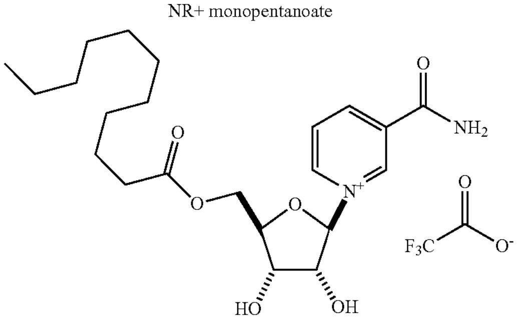

NR+ monoundecanoate

Additional exemplary NR analogues are described in, for example, Bioorg. Med. Chem. Lett. 2002, 12, 1135-1137; Franchetti et al., Bioorg. Med. Chem. Lett. 2004, 14, 4655-4658; and Yang, et al., Med. Chem. 2007, 50, 6458-6461.

US20180200275 describes that mixing NR with anthocyanin(s) or flavan-3-ol(s) of flavonoids forms positively-charged aggregating molecular forms through co-solvation and improves the oral absorption of NR through the stomach or intestine.

In particular embodiments, external factors include any compound including NR (e.g., NR chloride, NR bromide, OENR (O-ethyl nicotinamide riboside), TAENR (tri-O-acetyl O'-ethyl nicotinamide riboside), DMNR (N-dimethyl nicotinamide riboside), and ANR (N-allyl nicotinamide riboside)).

In particular embodiments, external factors include any compound that is subject to metabolism by the 5' nucleotidase CD73 that produces NR as a product. Examples of these compounds are described in, for example, Garavaglia et al, Biochemical Journal Dec. 14, 2011, 441(1) 131-141.

Compositions for Administration. NAMPT inhibitors and external factors for salvage pathways (collectively, physiologically active components) can be formulated alone or in combination into compositions for administration to subjects. Salts and/or pro-drugs of physiologically active components (PAC) can also be used.

A pharmaceutically acceptable salt includes any salt that retains the activity of the PAC and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes a PAC which is converted to a therapeutically active compound after administration, such as by cleavage of a PAC or by hydrolysis of a biologically labile group.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the PAC or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinositol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated including a powder mix of PAC and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salt.

Additionally, compositions can be formulated as sustained-release systems utilizing semipermeable matrices of solid polymers including at least one PAC. Various sustained-release materials have been established and are well known by those of ordinary skill in the art. Sustained-release systems may, depending on their chemical nature, release PAC following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Delaware), poly(vinyl alcohol) (PVA), Brij® (Croda Americas, Wilmington, Delaware), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Particular embodiments include formulation of PAC within hydrogels. Exemplary hydrogels include collagen hydrogels; type I collagen, fibrin, or a mixture thereof cross-linked, as the cross-linked state of these molecules in vivo; type I collagen hydrogels naturally cross-linked by lysyl oxidase-derived aldimine bonds (Sabeh et al., (2009) J Cell Biol 185:11-19); or other synthetic hydrogels as described in, for example, Rowe & Weiss (2008) Trends Cell Biol 18:560-574; Rowe & Weiss (2009) Annu Rev Cell Dev Biol 25:567-595; Egeblad et al., (2010) Curr Opin Cell Biol 22:697-706; Harunaga & Yamada (2011) Matrix Biol 30:363-368; Willis et al., (2013) J Microsc 251:250-260; and Gill et al. (2012) Cancer Res 72:6013-6023. In particular embodiments, a hydrogel refers to a network of polymer chains that are hydrophilic in which water or an aqueous medium is the dispersion medium. Particular embodiments may utilize a zwitterionic polymer as described in WO2016/040489.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

In particular embodiments, the compositions include PAC of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

In particular embodiments, PAC within a combination therapy are formulated into separate individual compositions. In particular embodiments, PAC combinations may be formulated into compositions together. When formulated together, the PAC may be included in the same amounts or in different amounts or ratios. For example, if one NAM PT inhibitor and one external factor are provided, these PAC could be included in the following exemplary ratios: 1:1, 2:1, 1:2, 5:1, 1:5, 10:1, 1:10, etc. If two NAMPT inhibitors and one external factor are provided, these PAC could be included in the following exemplary ratios: a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. If one NAMPT inhibitor and two external factors are provided, these PAC could be included in the following exemplary ratios: a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc.

Compositions disclosed herein can be formulated for administration by, for example, injection, infusion, perfusion, or lavage. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous injection.

Methods of Use. Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a cancer's development or progression.

A "prophylactic treatment" includes a treatment administered to a subject who does not display signs or symptoms of a cancer or displays only early signs or symptoms of a cancer such that treatment is administered for the purpose of diminishing or decreasing the risk of developing the cancer further. Thus, a prophylactic treatment functions as a preventative treatment against a cancer. In particular embodiments, prophylactic treatments reduce, delay, or prevent metastasis from a primary a cancer tumor site from occurring.

A "therapeutic treatment" includes a treatment administered to a subject who displays symptoms or signs of a cancer and is administered to the subject for the purpose of diminishing or eliminating those signs or symptoms of the cancer. The therapeutic treatment can reduce, control, or eliminate the presence or activity of the cancer and/or reduce control or eliminate side effects of the cancer.

Function as an effective amount, prophylactic treatment or therapeutic treatment are not mutually exclusive, and in particular embodiments, administered dosages may accomplish more than one treatment type.

In particular embodiments, therapeutically effective amounts provide therapeutic anti-cancer effects. Therapeutic anti-cancer effects include a decrease in the number of cancer cells, decrease in the number of metastases, a decrease in tumor volume, an increase in life expectancy, induced chemo- or radiosensitivity in cancer cells, inhibited angiogenesis near cancer cells, inhibited cancer cell proliferation, inhibited tumor growth, prevented or reduced metastases, prolonged subject life, reduced cancer-associated pain, and/or reduced relapse or re-occurrence of cancer following treatment.

A tumor is one type of cancerous tissue. A tumor refers to a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant or malignant.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of cancer, stage of cancer, previous or concurrent therapeutic interventions, idiopathy of the subject and route of administration.

Useful doses can range from 0.1 to 5 pg/kg or μg/kg or from 0.5 to 1 pg/kg μg/kg. In other examples, a dose can include 1 μg/kg, 15 μg/kg, 30 μg/kg, 50 μg/kg, 55 μg/kg, 70 μg/kg, 90 μg/kg, 150 μg/kg, 350 μg/kg, 500 μg/kg, 750 μg/kg, 1000 μg/kg, 0.1 to 5 mg/kg or from 0.5 to 1 mg/kg. In other non-limiting examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

The pharmaceutical compositions described herein can be administered by injection, inhalation, infusion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

In particular embodiments, compositions can be locally or regionally administered. For example, compositions can be administered in a surgical resection bed of an intra-cranial solid tumor. Compositions can be administered directly into solid tumors, for example in a hydrogel, as described above.

In particular embodiments, compositions can be administered to different portions or areas of the body and/or in different administration forms (e.g., oral and intravenous; oral and transdermal, etc.).

As indicated, in particular embodiments, an in vitro analysis of optimal response to a combination therapy disclosed herein can be assessed for personalized cancer cell killing. In these embodiments, a biopsy sample from a subject can be obtained. The subject's tissue can be assessed for NMRK and/or Myc expression and, if appropriate, tested against various combinations of NAMPT inhibitors and external factors. A high throughput automated platform can be used to analyze optimal therapies and/or dose concentrations based on the results of testing.

Particular embodiments include bringing a sample obtained from an individual subject into contact with a reagent suitable for determining the expression level of NMRK and/or Myc, e.g., a reagent or reagents suitable for determining the expression level using, e.g., flow cytometry, fluorescence-activated cell sorting (FACs), RT-qPCR, microarray analysis, ELISA, protein chips, mass spectrometry, or Western blotting. For example, in particular embodiments, the reagent may be an antibody suitable for determining the expression level of said one or more proteins using flow cytometry, fluorescence-activated cell sorting (FACs), ELISA or Western blotting. In particular embodiments, the reagent may be a pair or pairs of nucleic acid primers, suitable for determining the expression level of one or more of NMRK and/or Myc nucleic acids using RT-qPCR.

In particular embodiments, one member of a combination therapy can be administered before other members of the therapy. For example, injection of one member of a combination therapy can occur after a previously administered member has distributed through the body.

In particular embodiments, different amounts of members of a combination therapy are administered. For example, a NAMPT inhibitor and an external factor can be administered in the following exemplary ratios: 1:1, 2:1, 1:2, 5:1, 1:5, 10:1, 1:10, etc. If two NAMPT inhibitors and one external factor are provided, these members of a combination therapy could be administered in the following exemplary ratios: a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. If one NAMPT inhibitor and two external factors are provided, these members of a combination therapy could be administered in the following exemplary ratios: a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc.

In particular embodiments, members of a combination therapy may have different half-lives. Timing of administration and dosing schedules can be adjusted to account for this occurrence.

In particular embodiments, combination therapies described herein can be administered with other appropriate anti-cancer treatments, such as radiation, chemotherapy, or cell-based therapies.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN® from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-$HT_3$ receptor inhibitor (e.g., dolansetron, granisetron, ondansetron) with or without dexamethasone.

Combination treatment methods disclosed herein can be particularly well-suited to treat $NMRK^{low}$ and/or $Myc^{high}$ forms of central nervous system cancers including, for example, gliomas, low-grade gliomas, high-grade gliomas (e.g., Glioblastoma multiforme), ependymomas, and neuroblastomas. Other cancer types that can be particularly well-suited for treatment according to the current disclosure include $Myc^{high}$ forms of breast cancer, non-small cell lung cancer, small cell lung cancer, prostate cancer, colon cancer, and hepatocellular carcinoma.

Gliomas arise from astrocytes and account for 65% of all primary central nervous system tumors. Different types of glioma are classified according to their cell type of origin, their grade and their histological features. Types of gliomas include glioblastoma multiforme (GBM), low-grade glioma, ependymoma, astrocytomas, medulloblastoma, oligodendroglioma, choroid plexus papilloma, anaplastic astrocytoma, anaplastic oligodendroastrocytoma, and anaplastic oligodendroglioma. A class of proteins used as markers for gliomas and primitive neuroectodermal tumors include the cytoskeletal proteins, neurofilament (NF), glial fibrillary acidic protein (GFAP), intermediate filaments (IF), intermediate associated protein filament (IFAP), vimentin, nestin and keratins. These markers have been used to determine stages of differentiation along different cell lineages (see, e.g., Kleinert R. (1991) Acta Neuropathol 82:508-15).

Low-grade gliomas [WHO grade II] are typically well-differentiated and tend to exhibit benign tendencies. Advances in genome-wide technology have identified three molecular classes of low-grade gliomas that have superior correlations to outcomes than histologic grades. Of these classes, isocitrate dehydrogenase (IDH) mutations represent a particularly compelling target for precision imaging and therapy. Mutations in the IDH enzyme are the most common genetic alterations in World Health Organization Grade (WHO) grade II/III human gliomas. IDH mutations result in the neomorphic activity of the enzyme to produce the oncometabolite R-2-hydroxyglutarate (2HG). 2HG accumulates in IDH mutant gliomas and competitively inhibits a family of more than fifty □-ketoglutarate dependent enzymes, including many enzymes involved in gene regulation and cellular differentiation.

High-grade gliomas [WHO grade III or IV], such as Glioblastoma Multiforme are typically undifferentiated and frequently malignant. Glioblastoma multiforme (GBM) is the most frequent primary tumor of the central nervous system (CNS) and the most aggressive type of glioma. GBM is characterized by a diffuse and aggressive phenotype that is associated with rapid cellular proliferation, angiogenesis and necrosis. GBM is associated with significant intertumoral heterogeneity and as such the genomic profile of GBM has been well characterized. It is widely recognized that there are 4 subtypes of GBM as defined by their transcriptional profiles; classical, mesenchymal, neural and proneural. The classical GBM subtype is associated with a higher frequency of EGFR mutations and the absence of mutations in TP53. In contrast, mesenchymal GBM exhibit frequent mutations in NF1, PTEN and TP53 tumor suppressor genes, and correlates with a higher percentage of necrosis and inflammation. Neural GBM shares many of the mutations associated with the other subtypes, but is characterized by a genetic profile more similar to that of normal neurons. The fourth subtype, proneural, features mutations in TP53 as well as frequent mutations in IDH1 and PDGFRA. This subtype occurs particularly in younger patients and is associated with a trend towards prolonged survival compared to the other subtypes of GBM.

Ependymomas form in the central canal of the spinal cord and ventricular ependymal cells in the brain white matter or ependymal cells of the central nervous system as tumor nests and spread along the subarachnoid space. Common cytokines or their receptors linking tumors of astrocytomas, ependymomas and primitive neuroectodermal tumors have been identified as: interleukin (IL) IL-la, IL-1R1, IL-1R antagonist and transforming growth factor (TGF) TGF-β1 (Ilyin S. E., et al. (1998) Mol. Chem. Neuropathol. 33:125-137).

Neuroblastoma is a malignant cancer of the postganglionic sympathetic nervous system that derives from the neural crest cells during embryonic development. The majority of tumor cells present in neuroblastoma are N-type cells (neuroblastic), S-type cells (substrate adherent) and I-type cells (intermediate), each of which differ morphologically and biochemically. I-type cells are intermediate cells as these cells can differentiate into N-type as well as S-type neuroblastoma cells. I-type cells are considered as neuroblastoma stem cells since they are multipotent and differentiate to both N- or S-type of cells and because they express stem cell markers CD133 and c-kit (CD117). Neuroblastomas commonly express a selective increase in the gene copy number of the MYCN gene, found in fetal stages of brain development.

Kits. The current disclosure includes kits to assess a tumor as $NMRK^{low}$ and/or $Myc^{high}$ and/or to provide a combination therapy as disclosed herein. For example, in particular embodiments, the kits can include antibodies and/or primers and probes to detect expression levels of NMRK and/or Myc from a subject sample. In particular embodiments, the kits can include an NAMPT inhibitor and an external factor formulated for administration to a subject, either individually or in combination. In particular embodiments, the kit can include one or more reagents to collect a tissue sample from a subject and/or to determine if the tissue sample is $NRMK^{low}$ and/or $Myc^{high}$.

Screening Tools. The current disclosure includes the use of $NMRK^{low}$ cells as a screening tool to identify compounds useful according to the teachings of the current disclosure. For example, in particular embodiments, isogenic $NMRK^{low}$ cells and $NMRK^{+}$ cells can be exposed to test compounds and assessed for differential susceptibility to the compounds in the presence and absence of an external factor, such as NMN or NR. If the external factor reverses or ameliorates the cytoxicity of a compound in $NMRK^{+}$ cells, but not in $NMRK^{low}$ cells, then that compound would be appropriate for use in the combination therapies described herein. In particular embodiments, isogenic $NMRK^{low}$ cells and $NMRK^{+}$ cells can be GSC-0131 cells and GSC-0827 cells.

Exemplary Embodiments

1. A method of treating cancer in a subject in need thereof including administering a therapeutically effective amount of a nicotinamide phosphoribosyltransferase (NAMPT) inhibitor and an external factor to a subject thereby treating cancer in need the subject.
2. The method of embodiment 1, wherein the cancer is a nicotinamide riboside kinase (NMRK)'° w cancer.
3. The method of embodiment 1 or 2, wherein the cancer is a $Myc^{high}$ cancer.
4. The method of any of embodiments 1-3, wherein the NAMPT inhibitor includes FK866 ((E)-N-[4-(1-benzoyl-4-yl)-butyl]-3-(pyridin-3-yl) acrylamide), CHS-828 (N-[6-(4-chlorophenoxy)hexyl]-N'-cyano-N"-4-pyridinyl-guanidine, GNE-617 (N-(4-((3,5-difluorophenyl)sulfonyl)benzyl) imidazo[1,2-a]pyridine-6-carboxamide), GNE-618 (N-[[4-[[3-(Trifluoromethyl)phenyl]sulfonyl] phenyl]methyl]-1H-pyrazolo[3,4-b]pyridine-5-carboxamide), STF118804 (4-[5-Methyl-4-[[(4-methylphenyl)sulfonyl] methyl]-2-oxazolyl]-N-(3-pyridinylmethyl)benzamide), KPT-9274 ((E)-3-(6-aminopyridin-3-yl)-N-[[5-[4-(4,4-difluoropiperidine-1-carbonyl)phenyl]-7-(4-fluorophenyl)-1-benzofuran-2-yl]methyl]prop-2-enamide), and/or LSN3154567 (2-hydroxy-2-methyl-N-[1,2,3,4-tetrahydro-2-[2-(3-pyridinyl oxy)acetyl]-6-isoquinolinyl]-1-propane-sulfonamide.

5. The method of any of embodiments 1-4, wherein the NAMPT inhibitor includes a pyridyloxyacetyl tetrahydroisoquinoline compound; a 1,3-dihydro-2H-isoindole compound; a 4,5-dihydroisoxazole derivative compound; a 1,4-disubstituted triazole with substitution compound; a quinoxaline, quinazoline, quinoline compound; and/or a 4-{[(pyridin-3yl-methyl) aminocarbonyl] amino} benzene-sulfone derivative compound 6. The method of any of embodiments 1-5, wherein the external factor includes NMN and/or NR.
7. The method of any of embodiments 1-6, wherein the external factor includes NRH, NAR, and/or NARH.
8. The method of any of embodiments 1-7, wherein the external factor includes an NR analogue including NR chloride or a crystalline form of NR chloride.
9. The method of any of embodiments 1-8, wherein the crystalline form of NR chloride includes
3-carbamoyl-1-((2R,3R,4S,5R)-3,4-dihydroxy-5(hydroxymethy)tetrahydrofuran-2-yl)pyridin-1-ium(β-D-NR) chloride crystal,
3-carbamoyl-1-((2R,3R,4S,5R)-3,4-dihydroxy-5(hydroxymethy)tetrahydrofuran-2-yl)pyridin-1-ium(β-D-NR chloride methanolate crystal, and/or
3-carbamoyl-1-((2S,3R,4S,5R)-3,4-dihydroxy-5(hydroxymethyl)tetrahydrofuran-2-yl)pyridin-1-ium chloride.
10. The method of any of embodiments 1-9, wherein the external factor includes an NR analogue including
1-(2',3',5'-triacetyl-beta-D-ribofuranosyl)-1,4-dihydronicotinic acid and/or
1-(2',3',5'-triacetyl-beta-D-ribofuranosyl)-1,4-nicotinamide.
11. The method of any of embodiments 1-10, wherein the external factor includes an NR analogue including O-ethyl NR (OENR), tri-O-acetyl O'-ethyl NR (TAENR), N-dimethyl NR (DMNR), and/or N-allyl NR (ANR).
12. The method of any of embodiments 1-11, wherein the external factor includes an NR analogue including NRH triacetate, NRH triproprionate, NRH tributyrate, NRH triisobutyrate, NR+ tripentanoate, NR+ trihexanoate, NRH triethylcarbonate, NRH tribenzoate, NR+ monohexanoate, NRH monodecanoate, NRH monotetradecanoate, Nic mononucleotide (NMN), NR+ monooleate, NR+ monohexanoate, NR+ monononanoate, NR+ monododecanoate, NR+ monopentanoate, and/or NR+ monoundecanoate.
13. The method of any of embodiments 1-12, wherein the external factor includes NR or an NR analogue mixed with anthocyanin(s) or flavan-3-ol(s) of flavonoids.
14. The method of any of embodiments 1-13, wherein the cancer is a $NMRK^{low}$ and/or $Myc^{high}$ neuroblastoma, low grade glioma, glioblastoma, ependymoma, acute lymphocytic leukemia, chronic myeloid leukemia, esophageal cancer, non-small cell and small cell lung carcinoma, osteosarcoma, ovarian germ cell tumor, and pancreatic ductal carcinoma.
15. A combination therapy for treating cancer including an NAMPT inhibitor and an external factor.
16. The combination therapy of embodiment 15, wherein the NAMPT inhibitor includes
FK866 ((E)-N-[4-(1-benzoyl-4-yl)-butyl]-3-(pyridin-3-yl) acrylamide),
CHS-828 (N-[6-(4-chlorophenoxy)hexyl]-N'-cyano-N"-4-pyridinyl-guanidine,
GNE-617 (N-(4-((3,5-difluorophenyl)sulfonyl)benzyl) imidazo[1,2-a]pyridine-6-carboxamide),
GNE-618 (N-[[4-[[3-(Trifluoromethyl)phenyl]sulfonyl] phenyl]methyl]-1H-pyrazolo[3,4-b]pyridine-5-carboxamide),
STF118804 (4-[5-Methyl-4-[[(4-methylphenyl)sulfonyl] methyl]-2-oxazolyl]-N-(3-pyridinylmethyl)benzamide),
KPT-9274 ((E)-3-(6-aminopyridin-3-yl)-N-[[5-[4-(4,4-difluoropiperidine-1-carbonyl)phenyl]-7-(4-fluorophenyl)-1-benzofuran-2-yl]methyl]prop-2-enamide), and/or
LSN3154567 (2-hydroxy-2-methyl-N-[1,2,3,4-tetrahydro-2-[2-(3-pyridinyl oxy)acetyl]-6-isoquinolinyl]-1-propane-sulfonamide.
17. The combination therapy of embodiment 15 or 16, wherein the NAMPT inhibitor includes a pyridyloxyacetyl tetrahydroisoquinoline compound; a 1,3-dihydro-2H-isoindole compound; a 4,5-dihydroisoxazole derivative compound; a 1,4-disubstituted triazole with substitution compound; a quinoxaline, quinazoline, quinoline compound; and/or a 4-{[(pyridin-3yl-methyl) aminocarbonyl] amino} benzene-sulfone derivative compound
18. The combination therapy of any of embodiments 15-17, wherein the external factor includes NMN and/or NR.
19. The combination therapy of any of embodiments 15-18, wherein the external factor includes NRH, NAR, and/or NARH.
20. The combination therapy of any of embodiments 15-19, wherein the external factor includes an NR analogue including NR chloride or a crystalline form of NR chloride.
21. The combination therapy of any of embodiments 15-20, wherein the crystalline form of NR chloride includes
3-carbamoyl-1-((2R,3R,4S,5R)-3,4-dihydroxy-5(hydroxymethy)tetrahydrofuran-2-yl)pyridin-1-ium(β-D-NR) chloride crystal,
3-carbamoyl-1-((2R,3R,4S,5R)-3,4-dihydroxy-5(hydroxymethy)tetrahydrofuran-2-yl)pyridin-1-ium(β-D-NR chloride methanolate crystal, and/or
3-carbamoyl-1-((2S,3R,4S,5R)-3,4-dihydroxy-5(hydroxymethyl)tetrahydrofuran-2-yl)pyridin-1-ium chloride.
22. The combination therapy of any of embodiments 15-21, wherein the external factor includes an NR analogue including 1-(2',3',5'-triacetyl-beta-D-ribofuranosyl)-1,4-dihydronicotinic acid and/or 1-(2',3',5'-triacetyl-beta-D-ribofuranosyl)-1,4-nicotinamide.
23. The combination therapy of any of embodiments 15-22, wherein the external factor includes an NR analogue including O-ethyl NR (OENR), tri-O-acetyl O'-ethyl NR (TAENR), N-dimethyl NR (DMNR), and/or N-allyl NR (ANR).
24. The combination therapy of any of embodiments 15-23, wherein the external factor includes an NR analogue including NRH triacetate, NRH triproprionate, NRH tributyrate, NRH triisobutyrate, NR+ tripentanoate, NR+ trihexanoate, NRH triethylcarbonate, NRH tri benzoate, NR+ monohexanoate, NRH monodecanoate, NRH monotetradecanoate, Nic mononucleotide (NMN), NR+ monooleate, NR+ monohexanoate, NR+ monononanoate, NR+ monododecanoate, NR+ monopentanoate, and/or NR+ monoundecanoate.
25. The combination therapy of any of embodiments 15-24, wherein the external factor includes NR or an NR analogue mixed with anthocyanin(s) or flavan-3-ol(s) of flavonoids.
26. The combination therapy of any of embodiments 15-25, for use in the treatment of a $NMRK^{low}$ and/or $Myc^{high}$ cancer.
27. The combination therapy of embodiment 26, wherein the $NMRK^{low}$ and/or $Myc^{high}$ cancer is neuroblastoma, low grade glioma, glioblastoma, ependymoma, acute lymphocytic leukemia, chronic myeloid leukemia, esophageal cancer, non-small cell and small cell lung carcinoma, osteosarcoma, ovarian germ cell tumor, or pancreatic ductal carcinoma.

28. The combination therapy of any of embodiments 15-27, wherein the NAMPT inhibitor and the external factor are formulated as separate compositions for administration.

29. The combination therapy of any of embodiments 15-28, wherein the NAMPT inhibitor and the external factor are formulated as a single composition for administration.

30. A method including:

Incubating a population of $NMRK^{low}$ cells and a population of $NMRK^{+}$ cells with a test compound;

Assessing the population of $NMRK^{low}$ cells and the population of $NMRK^{+}$ cells for cytotoxicity based on exposure to the test compound;

If cytoxicity is observed in both populations, incubating a second population of $NMRK^{low}$ cells and a second population of $NMRK^{+}$ cells with the test compound and an external factor;

Assessing the second population of $NMRK^{low}$ cells and the second population of $NMRK^{+}$ cells for cytotoxicity based on exposure to the test compound and the external factor;

Identifying the test compound as a candidate for drug development if cytoxicity in the presence of the external factor is reduced in the $NMRK^{+}$ cells but not the $NMRK^{low}$ cells.

31. The method of embodiment 30, wherein the $NMRK^{low}$ cells are GSC-0827 cells.

32. The method of embodiment 30 or 31, wherein the $NMRK^{+}$ cells are GSC-0131 cells.

33. The method of any of embodiments 30-32, wherein the test compound is part of a chemical compound library.

34. The method of any of embodiments 30-33, wherein the external factor includes NMN and/or NR.

35. The method of any of embodiments 30-34, wherein the external factor includes NRH, NAR, and/or NARH.

36. The method of any of embodiments 30-35, wherein the external factor includes an NR analogue including NR chloride or a crystalline form of NR chloride.

37. The method of embodiment 36, wherein the crystalline form of NR chloride includes 3-carbamoyl-1-((2R,3R,4S,5R)-3,4-dihydroxy-5(hydroxymethy)tetrahydrofuran-2-yl)pyridin-1-ium(β-D-NR) chloride crystal, 3-carbamoyl-1-((2R,3R,4S,5R)-3,4-dihydroxy-5(hydroxymethy)tetrahydrofuran-2-yl)pyridin-1-ium(β-D-NR chloride methanolate crystal, and/or 3-carbamoyl-1-((2S,3R,4S,5R)-3,4-dihydroxy-5(hydroxymethyl)tetrahydrofuran-2-yl)pyridin-1-ium chloride.

38. The method of any of embodiments 30-37, wherein the external factor includes an NR analogue including 1-(2',3',5'-triacetyl-beta-D-ribofuranosyl)-1,4-dihydronicotinic acid and/or 1-(2',3',5'-triacetyl-beta-D-ribofuranosyl)-1,4-nicotinamide.

39. The method of any of embodiments 30-38, wherein the external factor includes an NR analogue including O-ethyl NR (OENR), tri-O-acetyl O'-ethyl NR (TAENR), N-dimethyl NR (DMNR), and/or N-allyl NR (ANR).

40. The method of any of embodiments 30-39, wherein the external factor includes an NR analogue including NRH triacetate, NRH triproprionate, NRH tributyrate, NRH triisobutyrate, NR+tripentanoate, NR+ trihexanoate, NRH triethylcarbonate, NRH tribenzoate, NR+ monohexanoate, NRH monodecanoate, NRH monotetradecanoate, Nic mononucleotide (NMN), NR+ monooleate, NR+ monohexanoate, NR+ mononononanoate, NR+ monododecanoate, NR+ monopentanoate, and/or NR+ monoundecanoate.

41. The method of any of embodiments 30-40, wherein the external factor includes NR or an NR analogue mixed with anthocyanin(s) or flavan-3-ol(s) of flavonoids.

42. Use of NMKR1 status as a biomarker to select a cancer treatment for a subject.

43. A method including:

Obtaining a cancer sample derived from a subject;

Assessing the cancer sample for an expression level of NM KR and/or Myc;

Treating the subject with a therapeutically effective amount of a NAMPT inhibitor and an external factor if the assessment reveals an $NMRK^{low}$ and/or a $Myc^{high}$ cancer.

44. The method of embodiment 43, wherein the NAMPT inhibitor includes

FK866 ((E)-N-[4-(1-benzoyl-4-yl)-butyl]-3-(pyridin-3-yl) acrylamide),

CHS-828 (N-[6-(4-chlorophenoxy)hexyl]-N'-cyano-N"-4-pyridinyl-guanidine,

GNE-617 (N-(4-((3,5-difluorophenyl)sulfonyl)benzyl) imidazo[1,2-a]pyridine-6-carboxamide), GNE-618 (N-[[4-[[3-(Trifluoromethyl)phenyl]sulfonyl] phenyl]methyl]-1H-pyrazolo[3,4-b]pyridine-5-carboxamide), STF118804 (4-[5-Methyl-4-[[(4-methylphenyl)sulfonyl] methyl]-2-oxazolyl]-N-(3-pyridinylmethyl)benzamide), KPT-9274 ((E)-3-(6-aminopyridin-3-yl)-N-[[5-[4-(4,4-difluoropiperidine-1-carbonyl)phenyl]-7-(4-fluorophenyl)-1-benzofuran-2-yl]methyl]prop-2-enamide), and/or LSN3154567 (2-hydroxy-2-methyl-N-[1,2,3,4-tetrahydro-2-[2-(3-pyridinyl oxy)acetyl]-6-isoquinolinyl]-1-propane-sulfonamide.

45. The method of embodiment 43 or 44, wherein the NAM PT inhibitor includes a pyridyloxyacetyl tetrahydroisoquinoline compound; a 1,3-dihydro-2H-isoindole compound; a 4,5-dihydroisoxazole derivative compound; a 1,4-disubstituted triazole with substitution compound; a quinoxaline, quinazoline, quinoline compound; and/or a 4-{[(pyridin-3yl-methyl) aminocarbonyl] amino} benzene-sulfone derivative compound 46. The method of any of embodiments 43-45, wherein the external factor includes NMN and/or NR.

47. The method of any of embodiments 43-46, wherein the external factor includes NRH, NAR, and/or NARH.

48. The method of any of embodiments 43-47, wherein the external factor includes an NR analogue including NR chloride or a crystalline form of NR chloride.

49. The method of any of embodiments 43-48, wherein the crystalline form of NR chloride includes 3-carbamoyl-1-((2R,3R,4S,5R)-3,4-dihydroxy-5(hydroxymethy)tetrahydrofuran-2-yl)pyridin-1-ium(8-D-NR) chloride crystal, 3-carbamoyl-1-((2R,3R,4S,5R)-3,4-dihydroxy-5(hydroxymethy)tetrahydrofuran-2-yl)pyridin-1-ium(8-D-NR chloride methanolate crystal, and/or
3-carbamoyl-1-((2S,3R,4S,5R)-3,4-dihydroxy-5(hydroxymethyl)tetrahydrofuran-2-yl)pyridin-1-ium chloride.

50. The method of any of embodiments 43-49, wherein the external factor includes an NR analogue including
1-(2',3',5'-triacetyl-beta-D-ribofuranosyl)-1,4-dihydronicotinic acid and/or
1-(2',3',5'-triacetyl-beta-D-ribofuranosyl)-1,4-nicotinamide.

51. The method of any of embodiments 43-50, wherein the external factor includes an NR analogue including O-ethyl NR (OENR), tri-O-acetyl O'-ethyl NR (TAENR), N-dimethyl NR (DMNR), and/or N-allyl NR (ANR).

52. The method of any of embodiments 43-51, wherein the external factor includes an NR analogue including NRH triacetate, NRH triproprionate, NRH tributyrate, NRH triisobutyrate, NR+ tripentanoate, NR+ trihexanoate, NRH triethylcarbonate, NRH tribenzoate, NR+ monohexanoate, NRH monodecanoate, NRH monotetradecanoate, Nic mononucleotide (NMN), NR+ monooleate, NR+ monohexanoate, NR+ monon준onanoate, NR+ monododecanoate, NR+ monopentanoate, and/or NR+ monoundecanoate.

53. The method of any of embodiments 43-52, wherein the external factor includes NR or an NR analogue mixed with anthocyanin(s) or flavan-3-ol(s) of flavonoids.

54. The method of any of embodiments 43-53, wherein the cancer sample is derived from a neuroblastoma, low grade glioma, glioblastoma, ependymoma, acute lymphocytic leukemia, chronic myeloid leukemia, esophageal cancer, breast cancer, prostate cancer, non-small cell lung cancer, small cell lung cancer, osteosarcoma, ovarian cancer, ovarian germ cell tumor, colon cancer, pancreatic cancer, pancreatic ductal carcinoma, or hepatocellular carcinoma.

55. Use of an expression change of a NAD pathway gene (or other regulatory event) as a biomarker to select a cancer treatment for a subject.

Figure 2:
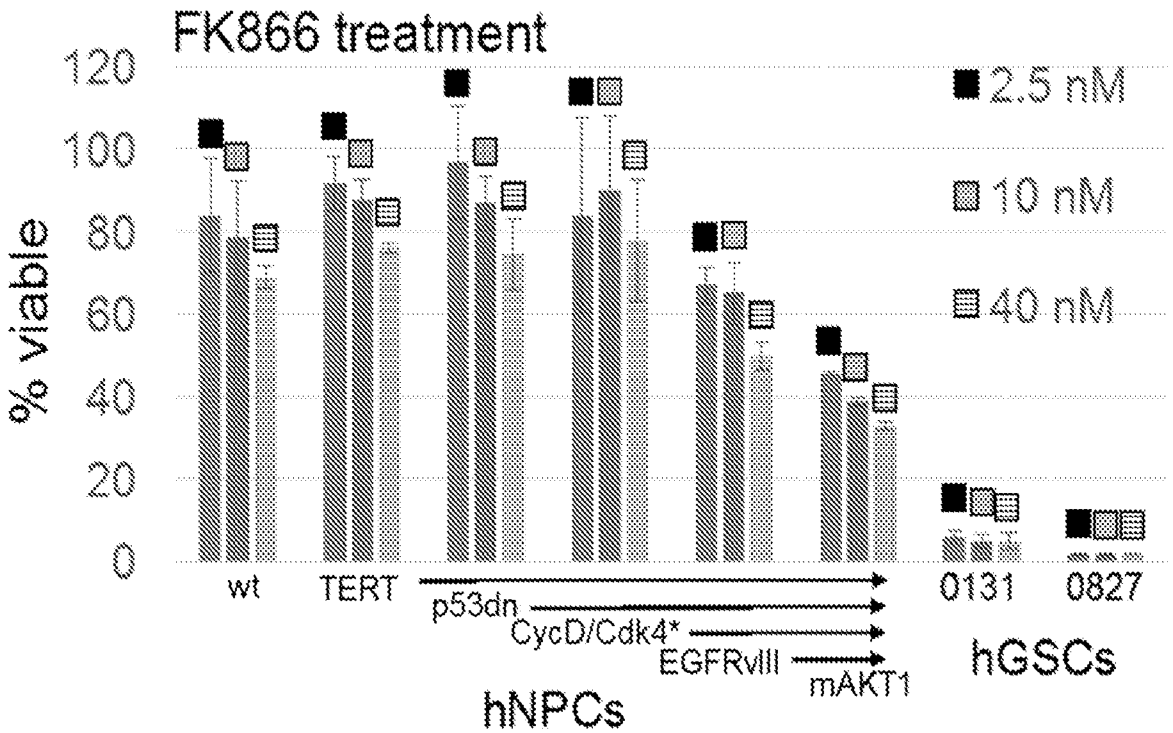
FIG. 2. Retest of NAMPT inhibitor FK866 in human neural stem cells (CB660) cells with various degrees of transformation and two glioblastoma (GBM) stem-like cells (GSC), showing GSC and transformation specificity (48 hrs; Cell titerglo assay; n=3).

Example 1. To Identify New Metabolic Vulnerabilities in Human GSCs, a Chemical Library screen was performed using 250 inhibitors of metabolic enzymes in two GSCs (0131 and 0827) and control hNPC-CB660 cells. Among the screen hits, FK866, an inhibitor of the NAD salvage enzyme NAMPT, was identified as having GSC-selective cytotoxicity (FIG. 2). To further explore this phenotype, an NAD salvage substrate, NMN was used, to bypass the requirement for NAMPT and rescue cytotoxicity. NMN is a substrate for the ectoenzyme CD73 (Ratajczak J et al., Nature communications. 2016; 7:13103), which generates NR, which is transported intracellular by equilibrative nucleoside transporters. (Nikiforov et al., J Biol Chem. 2011; 286(24): 21767-78.) Intracellular NR is phosphorylated by NMRK in a NAMPT-independent NAD salvage pathway.

While it was found that FK866-treated GSC-0131 cells could be rescued with NMN, GSC-0827 cells remained exquisitely sensitive to FK866. Puzzled, the expression of genes within known NAD salvage pathways was examined, and it was found that 0827 cells are devoid of NMRK1 expression (FIG. 3A). It was next demonstrated that LV-based ectopic expression of the NMRK1 open reading frame (ORF) in 0827 cells is sufficient to rescue FK866 sensitivity in the presence of NMN (FIG. 3B). Moreover, NMRK1 was deleted in 0131 cells via gene editing and NMN rescue was prevented (FIG. 3C). This demonstrates that NMRK1 is necessary and sufficient for rescue of NAMPT inhibition by NMN.

It was found that 5-20% of most tumor types (CNS and non-CNS) exhibit NMRK1$^{low}$ mRNA expression. Further, in looking for associations with oncogenic drivers, a significant negative correlation with MYCN and MYC expression for a variety of brain tumors and other cancers, including neuroblastoma, low grade glioma, GBM, ependymoma, ovarian cancer, and melanoma (FIG. 4) was found. Intriguingly, the 0827 GBM isolate has amplified MYC. hNSC-CB660 cells transduced with MYC exhibit 4-fold downregulation of NRMK1 mRNA expression (as well as a neighboring gene, OSTF1, which shares the NMRK1 promoter), suggesting MYC may be a negative transcriptional regulator of NMRK1 (data not shown). NAMPT inhibitors, including FK866 have exhibited dose-limiting toxicities in clinical trials, and rescue strategies have been proposed to improve their therapeutic index. (Olesen et al., Molecular cancer therapeutics. 2010; 9(6):1609-17; Holen et al., Investigational new drugs. 2008; 26(1):45-51; von Heideman et al., Cancer chemotherapy and pharmacology. 2010; 65(6):1165-72; Zabka et al., Toxicol Sci. 2015; 144(1):163-72.) The current disclosure provides an effective rescue strategy.

Methods. Cell culture. NSC and GSC lines were grown in NeuroCult NS-A basal medium (StemCell Technologies) supplemented with B27 (Thermo Fisher), N2 (2× stock in Advanced DMEM/F-12 (Fisher) with 25 μg/mL insulin (Sigma), 100 μg/mL apo-Transferrin (Sigma), 6 ng/mL progesterone (Sigma), 16 μg/mL putrescine (Sigma), 30 nM sodium selenite (Sigma), and 50 μg/mL bovine serum albumin (Sigma), and EGF and FGF-2 (20 ng/mL each) (Peprotech) on laminin (Sigma or Trevigen) coated polystyrene plates and passaged according to previously published protocols (Pollard et al., Cell Stem Cell. 2009; 4(6):568-80). Cells were detached from their plates using Accutase (Thermo Fisher). 293T (ATCC) cells were grown in 10% FBS/DMEM (Invitrogen).

Metabolic inhibitors screen protocol and data analysis. 230 metabolic inhibitors were screened in GSC lines (0131 and 827) and NSC CB660 cell line grown in 96-well optical bottom plates. After 24 hours, inhibitors were diluted in cell media and added to plated cells. Inhibitor concentration was based on IC 50 for the target enzymes, with 1× being the IC50 0.25× being the lower concentration and 5× being the higher concentration. Each concentration was tested in triplicate. After 48 hours, cell viability was measured via Cell-Titer-Glo. A z-score was established for each compound concentration, based on Untreated and Puromycin treated cells. Positive candidates were defined as compounds with a z-score less than that of CB660 cells. Positive candidates were rescreened to verify results.

NMN and NR Complementation studies. To verify if selectivity of NAMPT inhibition relied on downregulation of salvaging pathways, 827 cells were tested on cell viability in the presence of FK866 and the addition of NMN. It was demonstrated that NMN was sufficient to rescue GSC 0131 cells in the presence of FK866, but not GSC 0827 cells, suggesting that these cells downregulated NMRK1 and could therefore not benefit from supplementation of exogenous NMN.

Further validation required transfection of GSC 0827 cells with NMRK1 cDNA and demonstrated rescue of GSC 0827 cells with NMN in the presence of the NAMPT inhibitor, FK866. In addition, knockout of NMRK1 in GSC 0131 cells should replicate the effect of FK866 seen in GSC 0827 cells.

Summary of data from experiments examining NMRK1 status and function in NMKR1wt/normal cells (both NSC-CB660 and GSC 0131) and NMRK1$^{low}$ cells (GSC 0827).

| Cell Line | No drug control | FK-866 | FK-866 w/NMN |
|---|---|---|---|
| CB660 | + | + | + |
| GSC 0131 | + | − | + |
| GSC 0131 NMRK1 KO | + | − | − |
| GSC 0827 | + | − | − |
| GSC 0827 + NMRK1 | + | − | + |

"+" indicates similar viability compared to parental cells in "No drug control".
"−" indicates significantly diminished viability (as determined by Student's t-test).
This data indicates that NMRK1 expression is necessary for exogenous complementation with NMN in NMRK1wt/normal cells and sufficient to allow complementation in NMRK1$^{low}$ cells when ectopically expressed.

NMRK1 knockout. Using nucleofection (4D-Nucleofector; Amaxa) in combination with Cas9:sgRNA complexes (Synthego). Using the Synthego prediction software, 3 synthetic sgRNA guides were generated to give indel formation within the NMRK1 transcript. While individual guides had varying efficacy in nucleofection, it was found that a mixture yielded significant indel formation within GBM 0131 cells.

```
Sg Guide 1:
                                    (SEQ ID NO: 21)
UCUUGCGCUUUCCAUCCAGC;

Sg Guide 2:
                                    (SEQ ID NO: 22)
AGUGCUUGAAGCACUUAACA;

Sg Guide 3:
                                    (SEQ ID NO: 23)
UGAUGUCAGCCAUUUCCUGC.
```

Synthetic guides were mixed with recombinant cas9 and nucleofected using an Amaxa 96-well nucleofection system. Indel formation was highest with guides 1 and 2, and lowest with guide 3. Combining guides 1 and 2 yielded >90% indel formation.

NMRK1 Nucleofection Sequencing Primers:

```
F1:
                                    (SEQ ID NO: 24)
AAAAATGTTTCACTGTGGTTTGTC;

F2:
                                    (SEQ ID NO: 25)
AGAGTGTCTTGCGCTTTCCA;

R1:
                                    (SEQ ID NO: 26)
ACTGTGGTTTGTCAGCATTAGAGT;

R2:
                                    (SEQ ID NO: 27)
CAGCAGGAAATGGCTGACATC.
```

Cells were grown out on 10 cm dishes and genomic DNA harvested during plating for tests of NMN rescue of NAMPT Inhibition.

Lentiviral production. For virus production, lentiCRISPR v2 plasmids (Sanjana et al., Nat Methods. 2014; 11(8):783-4) were transfected using polyethylenimine (Polysciences) into 293T cells along with psPAX and pMD2.G packaging plasmids (Addgene) to produce lentivirus. Fresh media was added 24 hours later and viral supernatant harvested 24 and 48 hours after that. Lentivirus was used unconcentrated at an MOI<1.

Cloning of NMRK1 ORF and NMRK1 complementation studies. Initial attempts to replicate NMRK1 sequence from Brunello library revealed that transcript 1 variant (9:A6) of NMRK1 was not present, whereas transcript 2 (44:612), the inactive variant, could be replicated. This could be used as negative control for transfection purposes.

NMRK1 was then synthesized as a g-block based on HEK293T genomic DNA sequence:

```
                                          (SEQ ID NO: 28)
CGGGATCAACAAGTTTGTACAAAAAAGTTGGCATGAAAACATTTATCATT

GGAATCAGTGGTGTGACAAACAGTGGCAAAACAACACTGGCTAAGAATTT

GCAGAAACACCTCCCAAATTGCAGTGTCATATCTCAGGATGATTTCTTCA

AGCCAGAGTCTGAGATAGAGACAGATAAAAATGGATTTTTGCAGTACGAT

GTGCTTGAAGCACTTAACATGGAAAAAATGATGTCAGCCATTTCCTGCTG

GATGGAAAGCGCAAGACACTCTGTGGTATCAACAGACCAGGAAAGTGCTG

AGGAAATTCCCATTTTAATCATCGAAGGTTTTCTTCTTTTTAATTATAAG

CCCCTTGACACTATATGGAATAGAAGCTATTTCCTGACGATTCCATATGA

AGAATGTAAAAGGAGGAGGAGTACAAGGGTCTATCAGCCTCCAGACTCTC

CGGGATACTTTGATGGCCATGTGTGGCCCATGTATCTAAAGTACAGACAA

GAAATGCAGGACATCACATGGGAAGTTGTGTACCTGGATGGAACAAAATC

TGAAGAGGACCTCTTTTTGCAAGTATATGAAGATCTAATACAAGAACTAG

CAAAGCAAAAGTGTTTGCAAGTGACAGCATAACAAAACCCAAGTCACCAT

GTACTTGCCCAACTTTCTTGTACAAAGTGGTTGGTAAGC.
```

Insertion of the purified product into vector was accomplished via Gibson assembly using NEB HiFi DNA Assembly Master Mix Kit with BamHI pre-cut pLX304 vector for expression in GBM cell lines.

Once cloned into the pLX304 backbone, the NMRK1 expressing plasmid was prepared for nucleofection and introduced into GBM 0827 cell lines. Transfected cells were subsequently selected under Blasticidin. Cells were then used for tests of NAMPT inhibition and rescue with NMN.

RNA sequencing expression analysis. RNA was extracted using Direct-zol RNA MiniPrep Plus (Zymo Research). Total RNA integrity was checked and quantified using a 2200 TapeStation (Agilent). RNA-seq libraries were prepared using the KAPA Stranded mRNA-seq Kit with mRNA capture beads (KAPA Biosystems) according to the manufacturer's guidelines. Library size distributions were validated using a 2200 TapeStation (Agilent). Additional library QC, blending of pooled indexed libraries, and cluster optimization was performed using the Qubit 2.0 Fluorometer (Fisher). RNA-seq libraries were pooled and sequencing was performed using an Illumina HiSeq 2500 in Rapid Run mode employing a paired-end, 50 base read length (PE50) sequencing strategy. RNA-seq reads were aligned to the UCSC mm10 assembly using Tophat2 (Trapnell et al., Nat Protoc. 2012; 7(3):562-78) and counted for gene associations against the UCSC genes database with HTSeq (Anders et al., Bioinformatics. 2015; 31(2):166-9). Differential expression analysis was performed using R/Bioconductor package edgeR (Robinson et al., Bioinformatics. 2010; 26(1):139-40).

Prophetic Example 2. That FK866+ exogenous NR increases the therapeutic window for NMRK1$^{low}$ tumors will be confirmed. The combination of an inhibitor of the nicotinamide salvage enzyme, NAMPT, and a rescue precursor for nicotinamide synthesis, NR, is designed to preserve NAD levels in normal tissues, while depleting NAD to critical levels in tumor cells lacking NMRK1, a kinase required for converting NR to NMN (FIG. 1). While NMN, the phosphorylated form of NR, has been used for in vitro studies, NR has several advantages over NMN for in vivo administration. In contrast to NMN, NR is a form of vitamin $B_3$, has GRAS (generally recognized as safe) status from the FDA, and has been studied in several clinical trials. Both FK866 and NR are known to cross the blood-brain barrier. Formentini et al., Biochem Pharmacol. 2009; 77(10):1612-20; Chi et al., Curr Opin Clin Nutr Metab Care. 2013; 16(6):657-61.

The present disclosure encompasses all possible stereoisomers of described compounds, including both enantiomers and all possible diastereomers in substantially pure form and mixtures of both enantiomers in any ratio (including a racemic mixture of enantiomers) and mixtures of two or more diastereomers in any ratio, of the compounds described herein, and not only the specific stereoisomers as indicated by drawn structure or nomenclature. The specific recitation of the phrase "or stereoisomers thereof" or the like with respect to a compound in certain instances of the disclosure shall not be interpreted as an intended omission of any of the other possible stereoisomers of the compound in other instances of the disclosure where the compound is mentioned without recitation of the phrase "or stereoisomers thereof" or the like, unless stated otherwise or the context clearly indicates otherwise.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the selective killing of cancer cells over non-cancerous cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of treating a cancer in a subject comprising determining that the cancer's nicotinamide adenine dinucleotide (NAD) salvage pathway is unavailable by detecting that the cancer is $NMRK^{low}$ and $Myc^{high}$; and based on the determining, administering a therapeutically effective amount of a nicotinamide phosphoribosyltransferase (NAMPT) inhibitor and an external factor to the subject, wherein the NAMPT inhibitor is selected from the group consisting of FK866 ((E)-N-[4-(1-benzoyl-4-yl)-butyl]-3-(pyridin-3-yl) acrylamide), CHS-828 (N-[6-(4-chlorophenoxy)hexyl]-N'-cyano-N"-4-pyridinyl-guanidine, GNE-617 (N-(4-((3,5-difluorophenyl) sulfonyl)benzyl)imidazo[1,2-a]pyridine-6-carboxamide), GNE-618 (N-[[4-[[3-(Trifluoromethyl)phenyl]sulfonyl]phenyl]methyl]-1H-pyrazolo [3,4-b] pyridine-5-carboxamide), STF118804 (4-[5-Methyl-4-[((4-methylphenyl) sulfonyl]methyl]-2-oxazolyl]-N-(3pyridinylmethyl) benzamide), KPT-9274 ((E)-3-(6-aminopyridin-3-yl)-N-[[5-[4-(4,4-difluoropiperidine-1-carbonyl) phenyl]-7-(4-fluorophenyl)-1-benzofuran-2-yl] methyl]prop-2-enamide), and LSN3154567 (2-hydroxy-2-methyl-N-[1,2,3,4-tetrahydro-2-[2-(3-pyridinyl oxy)acetyl]-6-isoquinolinyl]-1-propane-sulfonamide, and the external factor is selected from the group consisting of nicotinamide mononucleotide (NMN), nicotinamide riboside (NR), reduced NR (NRH), nicotinic acid riboside (NAR), reduced nicotinic acid ribo side (NARH), NR chloride, 1-(2',3',5'-triacetyl-beta-D-ribofuranosyl)-1,4-dihydronicotinic acid, 1-(2',3',5'-triacetyl-beta-D-ribofuranosyl)-1,4-nicotinamide, O-ethyl NR (OENR), tri-O-acetyl O'-ethyl NR (TAENR), N-dimethyl NR (DMNR), N-allyl NR (ANR), NRH triacetate, NRH triproprionate, NRH tributyrate, NRH triisobutyrate, NR+ tripentanoate, NR+ trihexanoate, NRH triethylcarbonate, NRH tribenzoate, NR+ monohexanoate, NRH monodecanoate, NRH monotetradecanoate, Nic mononucleotide (NMN), NR+ monooleate, NR+ monohexanoate, NR+ monononanoate, NR+ monododecanoate, NR+ monopentanoate, and NR+ monoundecanoate thereby treating cancer in the subject.

2. The method of claim 1, wherein the NAMPT inhibitor comprises FK866 ((E)-N-[4-(1-benzoyl-4-yl)-butyl]-3-(pyridin-3-yl) acrylamide) and the external factor comprises nicotinamide mononucleotide (NMN) and/or nicotinamide riboside (NR).

3. The method of claim 1, wherein the external factor comprises nicotinamide mononucleotide (NMN), nicotinamide riboside (NR), or reduced NR (NRH).

4. The method of claim 1, wherein the external factor comprises NR chloride, 1-(2',3',5'-triacetyl-beta-D-ribofuranosyl)-1,4-dihydronicotinic acid, 1-(2',3',5'-triacetyl-beta-D-ribofuranosyl)-1,4-nicotinamide, O-ethyl NR (OENR), tri-O-acetyl O'-ethyl NR (TAENR), N-dimethyl NR (DMNR), N-allyl NR (ANR), NRH triacetate, NRH tripropionate, NRH tributyrate, NRH triisobutyrate.

5. The method of claim 1, wherein the external factor is mixed with anthocyanin(s) or flavan-3-ol(s) of flavonoids.

6. The method of claim 1, wherein the NAMPT inhibitor and the external factor are formulated as separate compositions for administration.

7. The method of claim 1, wherein the NAMPT inhibitor and the external factor are formulated as a single composition for administration.

8. The method of claim 1, wherein the cancer comprises neuroblastoma, low grade glioma, glioblastoma, or ependymoma.

9. The method of claim 1, further comprising determining an oligodendrocyte transcription factor 2 (OLIG2) expression level for the subject.

10. The method of claim 1, further comprising determining a programmed cell death ligand 1 (PD-L1) expression level for the subject.

* * * * *